US012661514B2

(12) United States Patent
Case et al.

(10) Patent No.: US 12,661,514 B2
(45) Date of Patent: Jun. 23, 2026

(54) ELECTRODE CHARACTERIZATION FOR PROGRAMMING GUIDANCE

(71) Applicant: Medtronic, Inc., Minneapolis, MN (US)

(72) Inventors: Michelle A. Case, Blaine, MN (US); Jadin C. Jackson, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 514 days.

(21) Appl. No.: 17/650,038

(22) Filed: Feb. 4, 2022

(65) Prior Publication Data

US 2022/0266026 A1     Aug. 25, 2022

Related U.S. Application Data

(60) Provisional application No. 63/152,957, filed on Feb. 24, 2021.

(51) Int. Cl.
*A61N 1/36* (2006.01)
*A61N 1/05* (2006.01)
*A61B 1/05* (2006.01)

(52) U.S. Cl.
CPC ....... *A61N 1/36139* (2013.01); *A61N 1/0534* (2013.01); *A61N 1/36185* (2013.01)

(58) Field of Classification Search
CPC .............. A61N 1/36139; A61N 1/0534; A61N 1/37235; A61N 1/36185; A61N 1/36135
See application file for complete search history.

(56) References Cited

U.S. PATENT DOCUMENTS

| 8,849,392 B2 | 9/2014 | Lozano |
| 8,868,173 B2 | 10/2014 | Nelson et al. |

(Continued)

FOREIGN PATENT DOCUMENTS

| WO | 2003043690 A1 | 5/2003 |
| WO | 2017158067 A1 | 9/2017 |
| WO | 2017203301 A1 | 11/2017 |

OTHER PUBLICATIONS

Im, C., Seo, JM. A review of electrodes for the electrical brain signal recording. Biomed. Eng. Lett. 6, 104-112 (2016). https://doi.org/10.1007/s13534-016-0235-1 (Year: 2016).*

(Continued)

*Primary Examiner* — Pamela M. Bays
*Assistant Examiner* — Christine Sison
(74) *Attorney, Agent, or Firm* — Shumaker & Sieffert, P.A.

(57) ABSTRACT

A system includes processing circuitry configured to determine, for each electrode combination of a plurality of electrode combinations, a metric based on a sensed electrical signal from the electrode combination. The processing circuitry is further configured to determine, for each electrode of a plurality of electrodes, a subset of electrode combinations of the plurality of electrode combinations, each electrode combination of the subset of electrode combinations comprising the electrode, wherein the subset of electrode combinations comprises at least two electrode combinations. The processing circuitry is further configured to determine, for each electrode of the plurality of electrodes, a composite metric based on the metrics of the subset of electrode combinations. The processing circuitry is further configured to determine, select, based on the composite metrics of the plurality of electrodes, at least one electrode for at least one of sensing electrical signals or delivering electrical stimulation.

19 Claims, 11 Drawing Sheets

(56) References Cited

U.S. PATENT DOCUMENTS

| | | | |
|---|---|---|---|
| 9,498,628 | B2 | 11/2016 | Kaemmerer et al. |
| 9,814,885 | B2 | 11/2017 | Molnar et al. |
| 10,857,364 | B1 | 12/2020 | Soin |
| 11,045,652 | B2 | 6/2021 | Jackson et al. |
| 11,135,429 | B2 | 10/2021 | Panken et al. |
| 11,318,296 | B2 | 5/2022 | Xiao et al. |
| 2008/0004674 | A1* | 1/2008 | King .................... A61N 1/0553 607/46 |
| 2011/0144715 | A1* | 6/2011 | Molnar ............. A61N 1/36185 607/45 |
| 2014/0213926 | A1 | 7/2014 | Vaidyanathan |
| 2016/0120432 | A1* | 5/2016 | Sridhar ................ A61B 5/6898 600/544 |
| 2017/0259064 | A1 | 9/2017 | Wu et al. |
| 2018/0280699 | A1 | 10/2018 | Arlotti et al. |
| 2019/0030321 | A1 | 1/2019 | Tinkhauser et al. |
| 2019/0126029 | A1 | 5/2019 | Cheeran et al. |
| 2019/0134401 | A1* | 5/2019 | Schouenborg ..... A61N 1/36132 |
| 2019/0143120 | A1 | 5/2019 | Sinclair et al. |
| 2020/0129757 | A1 | 4/2020 | Xiao et al. |
| 2020/0147364 | A1* | 5/2020 | Gani .................. A61N 1/37247 |
| 2020/0338351 | A1 | 10/2020 | Panken et al. |
| 2022/0032059 | A1 | 2/2022 | Molina et al. |
| 2022/0032063 | A1 | 2/2022 | Molina et al. |
| 2022/0062640 | A1 | 3/2022 | Raike et al. |
| 2022/0126100 | A1 | 4/2022 | Jackson et al. |

OTHER PUBLICATIONS

Ince et al., "Selection of Optimal Programming Contacts Based on Local Field Potential Recordings Form Subthalamic Nucleus in Patients with Parkinson's Disease," NIH Public Access, Neurosurgery, vol. 67, No. 2, doi:10.1227/01.NEU.0000372091.64824.63, Aug. 2010, pp. 390-397.

Tinkhauser et al., "Directional Local Field Potentials: A Tool to Optimize Deep Brain Stimulation," Wiley Online, Movement Disorders, vol. 00, No. 00, DOI: 10.1002/mds.27215, Oct. 3, 2017, 6 pp.

U.S. Appl. No. 17/410,268, filed Aug. 24, 2021, naming inventors Jackson et al.

U.S. Appl. No. 17/651,500, filed Feb. 17, 2022, naming inventors Jackson et al.

Advisory Action from U.S. Appl. No. 17/462,676 dated Apr. 4, 2024, 3 pp.

Response to Final Office Action dated Jan. 18, 2024 from U.S. Appl. No. 17/462,676, filed Mar. 18, 2024, 13 pp.

Extended Search Report from counterpart European Application No. 22158296.8 dated Jul. 22, 2022, 5 pp.

Final Office Action from U.S. Appl. No. 17/462,676 dated Jan. 18, 2024, 16 pp.

Office Action from U.S. Appl. No. 17/462,676 dated Aug. 9, 2023, 16 pp.

Response to Office Action dated Aug. 9, 2023 from U.S. Appl. No. 17/462,676, filed Nov. 9, 2023, 13 pp.

Office Action from U.S. Appl. No. 17/462,676 dated Jun. 14, 2024, 17 pp.

Response to Office Action dated Jun. 14, 2024 from U.S. Appl. No. 17/462,676, filed Sep. 16, 2024, 13 pp.

Advisory Action from U.S. Appl. No. 17/462,676 dated Mar. 27, 2025, 3 pp.

Notice of Allowance from U.S. Appl. No. 17/462,676 dated May 14, 2025, 7 pp.

Final Office Action from U.S. Appl. No. 17/462,676 dated Jan. 10, 2025, 17 pp.

Response to Final Office Action dated Jan. 10, 2025 from U.S. Appl. No. 17/462,676, filed Mar. 7, 2025, 13 pp.

* cited by examiner

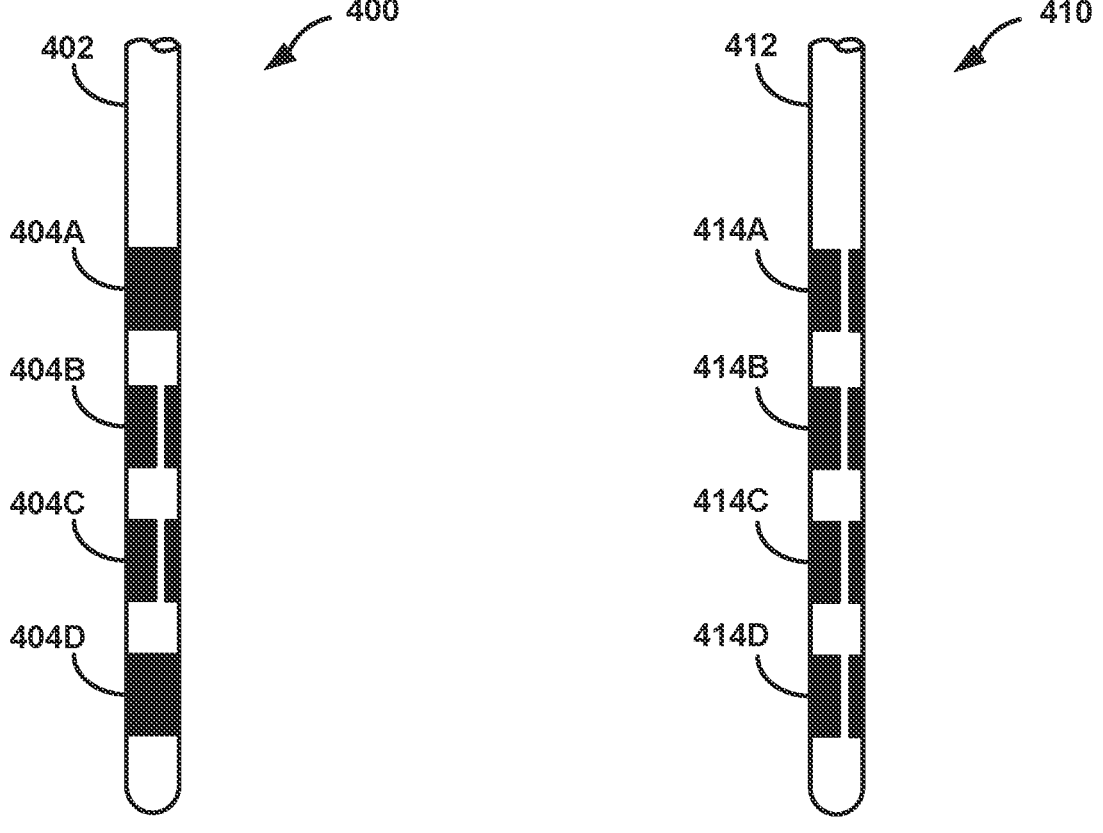
FIG. 4A                  FIG. 4B

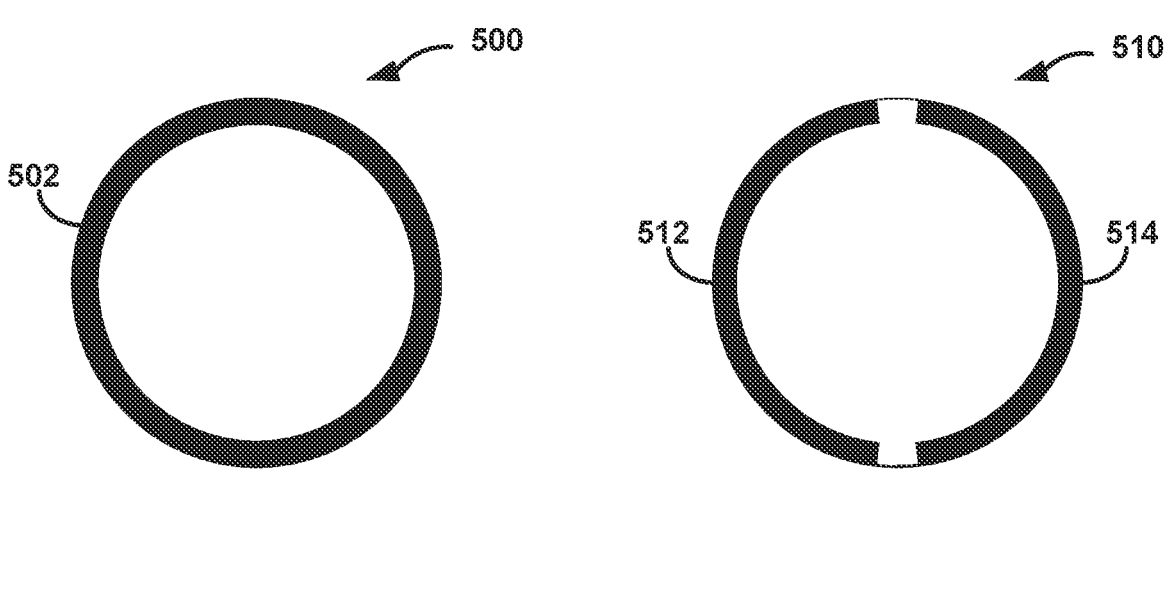
FIG. 5A                    FIG. 5B
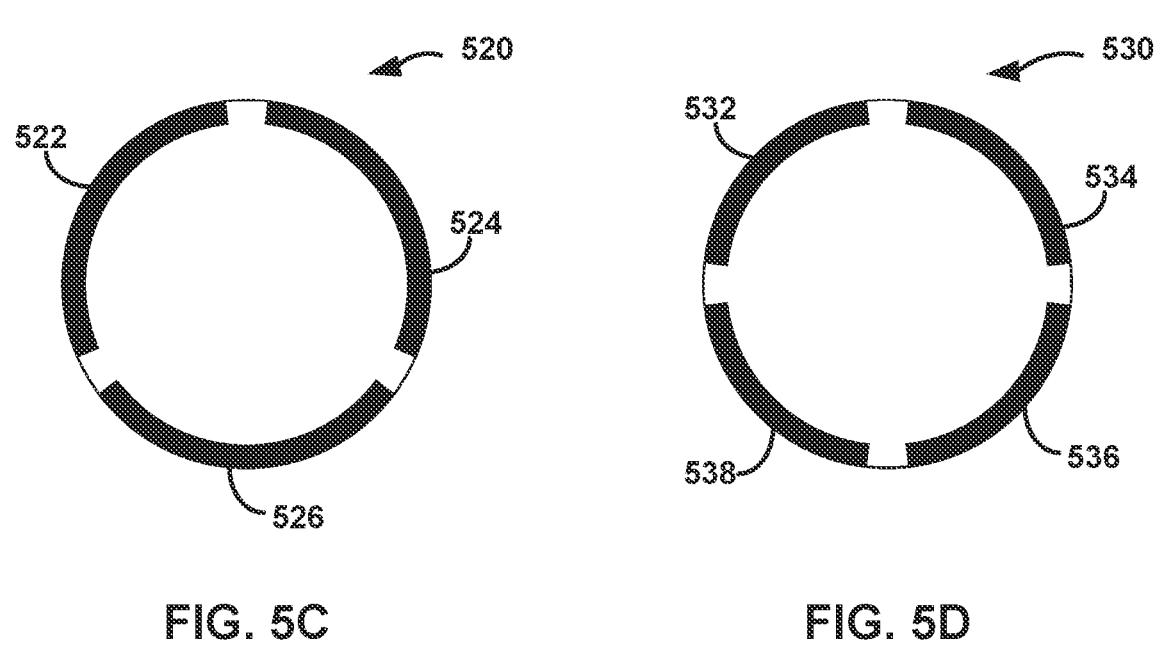
FIG. 5C                    FIG. 5D

ELECTRODE CHARACTERIZATION FOR PROGRAMMING GUIDANCE

This application claims the benefit of U.S. Provisional Application Ser. No. 63/152,957, filed Feb. 24, 2021, the entire content of which is incorporated herein by reference.

TECHNICAL FIELD

The disclosure relates to medical devices, and more specifically, sensing electrical signals from a patient.

BACKGROUND

Implantable medical devices (IMDs), such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, that may be deployed by medical leads and/or on a housing of the electrical stimulator. In some therapy systems, therapy may be delivered via particular combinations of the electrodes carried by leads and/or by the housing of the electrical stimulator.

During a programming session, that may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples where electrical stimulation is delivered in the form of electrical pulses, the therapy parameters may include an electrode configuration including an electrode, an electrode combination, electrode polarities, an amplitude (e.g., a current or voltage amplitude), a pulse width, and a pulse rate.

SUMMARY

In general, the disclosure is directed to devices, systems, and methods for utilizing sensed electrical signals, such as local field potentials (LFPs) in the brain, to identify at least one electrode on an implantable lead that is closest to a target region of tissue (e.g., of the subthalamic nucleus (STN)). Such a region may generate signals of interest (e.g., beta waves that are indicative of areas of the brain causing Parkinson's tremors). In this manner, the system may sense electrical signals between different combinations of electrodes. The system may then generate information regarding these signals and inform the implanting physician of these signals and/or recommend a subset of electrodes for sensing signals and/or delivering electrical stimulation.

The sensed signals may be between electrodes (e.g., bipolar sensing) at different positions around the perimeter of a medical lead and/or electrodes at different axial positions along the length of the medical lead. The sensed signals may be LFPs or derived from LFPs that are intrinsic to the patient or evoked by a stimulus. The system may then determine, for each respective electrode, a composite metric based on the sensed signals between multiple electrode combinations that each include the respective electrode (e.g., a common electrode to the multiple electrode combinations). The physician, or the system, may then select, based on the composite metrics or at least some electrodes, one or more electrode combinations and/or other stimulation parameters for directional stimulation or sensing.

In one example, this disclosure describes a system including processing circuitry configured to determine, for each respective electrode combination of a plurality of electrode combinations, a respective metric based on a sensed electrical signal from the respective electrode combination. The processing circuitry is further configured to determine, for each respective electrode of a plurality of electrodes, a subset of electrode combinations of the plurality of electrode combinations, each electrode combination of the subset of electrode combinations comprising the respective electrode, wherein the subset of electrode combinations comprises at least two electrode combinations. The processing circuitry is further configured to determine, for each respective electrode of the plurality of electrodes, a respective composite metric based on the respective metrics of the subset of electrode combinations. The processing circuitry is further configured to select, based on the respective composite metrics of the plurality of electrodes, at least one electrode for at least one of sensing electrical signals or delivering electrical stimulation.

In another example, this disclosure describes a method that comprises determining, by processing circuitry and for each respective electrode combination of a plurality of electrode combinations, a respective metric based on a sensed electrical signal from the respective electrode combination. The method further comprises determining, by processing circuitry and for each respective electrode of a plurality of electrodes, a subset of electrode combinations of the plurality of electrode combinations, each electrode combination of the subset of electrode combinations comprising the respective electrode, wherein the subset of electrode combinations comprises at least two electrode combinations. The method further comprises determining, by processing circuitry and for each respective electrode of the plurality of electrodes, a respective composite metric based on the respective metrics of the subset of electrode combinations. The method further comprises selecting, by processing circuitry and based on the respective composite metrics of the plurality of electrodes, at least one electrode for at least one of sensing electrical signals or delivering electrical stimulation.

In another example, this disclosure describes a non-transitory computer-readable medium comprising instructions that, when executed, cause processing circuitry to determine, for each respective electrode combination of a plurality of electrode combinations, a respective metric based on a sensed electrical signal from the respective electrode combination. The instructions further cause processing circuitry to determine, for each respective electrode of a plurality of electrodes, a subset of electrode combinations of the plurality of electrode combinations, each electrode combination of the subset of electrode combinations comprising the respective electrode, wherein the subset of electrode combinations comprises at least two electrode combinations. The instructions further cause processing circuitry to determine, for each respective electrode of the plurality of electrodes, a respective composite metric based on the respective metrics of the subset of electrode combinations. The instructions further cause processing circuitry to select, based on the respective composite metrics of the plurality of electrodes, at least one electrode for at least one of sensing electrical signals or delivering electrical stimulation.

The details of one or more examples are set forth in the accompanying drawings and the description below. Other features, objects, and advantages will be apparent from the description, drawings, and claims.

BRIEF DESCRIPTION OF DRAWINGS

FIGS. 4A and 4B are conceptual diagrams of example leads with respective electrodes carried by the medical lead.

FIGS. 5A, 5B, 5C, and 5D are conceptual diagrams of example electrodes disposed around a perimeter of a lead at a particular longitudinal location.

DETAILED DESCRIPTION

Figure 1:
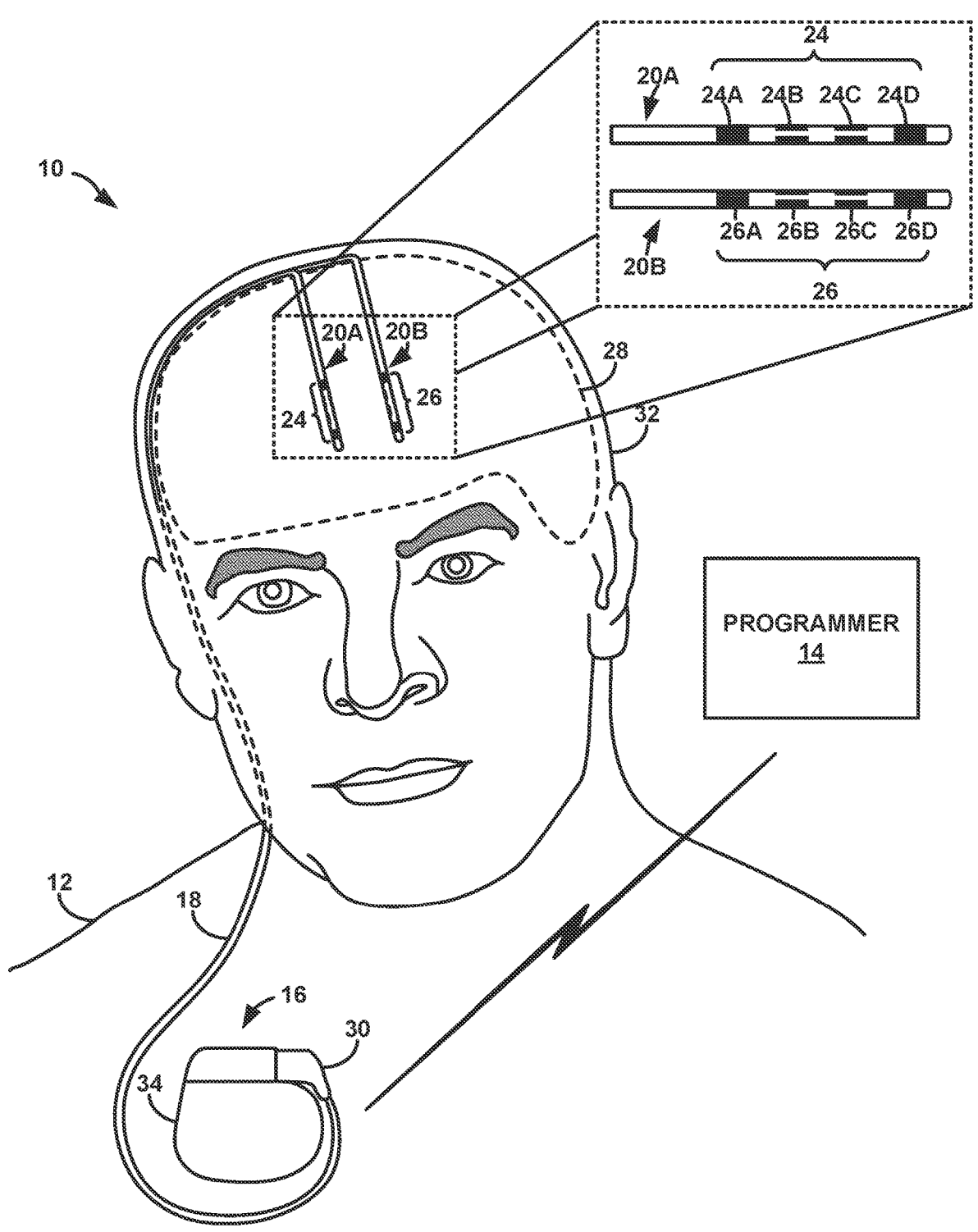
FIG. 1 is a conceptual diagram illustrating an example deep brain stimulation (DBS) system configured to deliver electrical stimulation therapy to a tissue site within a brain of a patient.

In general, the disclosure is directed to utilizing sensed electrical signals, such as LFPs within the brain, to identify at least one electrode on an implantable lead that is closest to a target region of tissue (e.g., the STN) and that may be appropriate for sensing electrical signals and/or delivering electrical stimulation.

Many brain disorders may be associated with abnormal brain function. In one example, Parkinson's Disease (PD) is a progressive neuro-degenerative disorder characterized by the depletion of dopaminergic neurons in the basal ganglia-thalamo-cortical network. As PD progresses, the manifestations of the disease may include one or more of the characteristic motor dysfunctions that include one or more of akinesia, bradykinesia, rigidity, and tremor. In some examples, deep brain stimulation (DBS) therapy may be used to deliver electrical stimulation to treat motor symptoms in medication-refractory PD patients. In some examples, DBS therapy may involve the unilateral or bilateral implantation of one or more leads into the brain to deliver electrical stimulation to target structures in the basal ganglia.

In general, unipolar sensing or bipolar sensing may be used to select effective simulation parameters for DBS therapy. For both unipolar sensing and bipolar sensing, electrical signals are sensed (e.g., measured) across one or more electrode combinations of electrodes where at least one electrode is an anode and at least one electrode is a cathode. Metrics for appropriate delivery of electrical stimulation may be generated based on the electrical signals measured by the electrode combination.

Regardless of which sensing technique is used (e.g., unipolar sensing, bipolar sensing, etc.), the selection of effective stimulation parameters for DBS therapy may be time-consuming for both the clinician (e.g., a physician, nurse, or technician) and the patient. As such, it may be desirable to reduce the amount of time consumed to select stimulation parameters. In addition, the trial-and-error approach for determining an appropriate electrode, electrode combinations and/or other stimulation parameters may subject the patient to undesirable side effects during this process.

In addition, a clinician may need to provide therapy to the patient requiring identifying one or more specific electrodes on an implantable lead appropriate for delivering electrical stimulation (e.g., the electrode on the implantable lead that is closest to a target region of tissue). However, metrics for appropriate delivery of electrical stimulation based on electrical signals are, in general, associated with the electrode combination and not the specific electrodes (e.g., anode electrode or cathode electrode) included in the electrode combination. Thus, generating metrics associated with respective electrodes, and thus identifying one or more specific electrodes appropriate for delivering electrical stimulation, may be desirable but difficult.

According to techniques described herein, a system may determine a composite metric for each electrode of a plurality of electrodes based on respective metrics of a subset of electrode combinations. The system may then select at least one electrode for at least one of sensing electrical signals or delivering electrical stimulation. In some examples, this information may be presented to a clinician to allow for selection of parameter values for stimulation (e.g., selection of the electrode and/or the electrode combination closest to a target region of tissue (e.g., the STN)).

As used herein, the term "axial" is used in connection with the length of an object (e.g., medical lead). For example, an axial electrode of a medical lead is an electrode located along the length of the medical lead. The term "axial" is intended to have this meaning regardless of the curvature or other property besides length of the object. As used herein, the term "perimeter" is used to describe the direction orthogonal to the axial direction of the lead. For example, a circumferential electrode of a medical lead is an electrode located at a specific circumferential position around the perimeter of the medical lead when the medical lead has a generally cylindrical shape.

In some examples, the sensed signals may be between different electrodes at different position around the perimeter of a medical lead or different electrodes at different axial positions along the length of the same medical lead (e.g., bipolar sensing). Monopolar sensing may be utilized in other examples. For example, monopolar sensing may be between a lead electrode and a remote electrode (e.g., one or more electrodes located on a different lead or housing of the IMD at a sufficient distance from the desired sensing location). Monopolar sensing may be utilized for sensing between electrodes of a lead that only has a single axial level of electrodes at different circumferential positions, in one example. In some examples, the techniques herein may enable a system to use bipolar sensing to determine composite metrics of electrodes and select an electrode for sensing, and then the system may use the selected electrode with monopolar sensing to sense signals from the patient.

In any case, the system, may determine a composite metric for an electrode based on a metric of a subset of electrode combinations in which the electrode is included. Additionally, the system may determine a composite metric for a plurality of electrodes in the same manner. This information may then be used to program stimulation more effectively and in less time than using other trial-and-error approaches.

For example, a Beta rhythm may be localized with the dorsal STN. In this example, it may be helpful to identify the electrode that is closest to this oscillatory region of the brain. In accordance with techniques described herein, the system may use a plurality of electrode combinations to sense electrical signals (e.g., by generating spectral power characteristics for one or more frequencies of the electrical signal) and determine, for each respective electrode combination of the plurality of electrode combinations, a respective metric based on a sensed electrical signal from the respective electrode combination.

The system may determine, for each respective electrode of a plurality of electrodes, a subset of electrode combinations of the plurality of electrode combinations, each electrode combination of the subset of electrode combinations comprising the respective electrode, wherein the subset of electrode combinations comprises at least two electrode combinations. The system may then determine, for each respective electrode of the plurality of electrodes, a respective composite metric based on the respective metrics of the subset of electrode combinations. The system may then select, based on the respective composite metrics of the plurality of electrodes, at least one electrode for at least one of sensing electrical signals or delivering electrical stimulation. For example, the system may select the electrode with the largest composite metric, as such a metric may be indicative of proximity to the region of the brain emitting the sensed electrical signal.

Thus, the system may use electrical signals sensed by a plurality of electrode combinations to determine metrics for a subset of electrode combinations (i.e., the electrode combinations in which a common electrode is included), and then determine a composite metric for the common electrode based on the metrics for the subset of electrode combinations. Each electrode combination of the subset of electrode combinations may overlap with at least one common electrode.

The metrics for the electrode combinations, and thus the subset of electrode combinations as well, may be based on signal strength of sensed LFPs, spectral power of a Beta frequency band within the sensed LFPs, or any other appropriate electrical signal generated by the brain. The system may then use the metrics for the electrode combinations in which the specific electrode is included to determine a composite metric for the specific electrode. Similarly, the composite metric may be based on signal strength of sensed LFPs, spectral power of a Beta frequency band within the sensed LFPs, or any other appropriate electrical signal generated by the brain. For example, the system may average the metrics for all electrode combinations of the subset of electrode combinations having the common electrode and assign the average as the composite metric for the one common electrode. The system may then repeat this process as many times as necessary to determine composite metrics of a plurality of electrodes (e.g., a composite metric for each corresponding electrode of the plurality of electrodes carried by the medical lead). In some examples, the system may determine the composite metrics of fewer than all electrodes carried by the lead. The system may exclude some electrode based on known implant location, electrode size, electrode shape, or some other characteristic.

As discussed above, the composite metric for each electrode may be determined by averaging the metrics for the corresponding subset of electrode combinations that each include the respective electrode. The average may be a mean, median, mode, or some other mathematical operation or algorithm for determining a value representative of the metrics for the subset of electrode combinations. For example, the average may be a weighted average, which may involve weighing the metrics for electrode combinations in which an electrode is closer to the common electrode greater than the metrics for electrode combinations in which an electrode is further from the common electrode. For example, if the common electrode is 2 mm from one electrode in a first electrode combination and the common electrode is 4 mm from another electrode in a second electrode combination, the metric for the first electrode combination in which the electrodes are closer together may be given a greater weight for determining the composite metric. In other examples, the composite metric may be determined by another mathematical operation or algorithm.

In some examples, the system may identify the electrode with the highest composite metric. Such information may be helpful because the composite metric may indicate the strength of the electrical signal (e.g., Beta waves) sensed by the electrode, which in turn may indicate proximity to a target region of tissue. For example, an electrode with the highest composite metric may be the electrode sensing the strongest electrical signal, which may indicate that the electrode's circumferential position (e.g., in the case of a generally cylindrical medical lead) around the perimeter of the medical lead and the identified electrode's axial position along the length of the medical lead may be closest to the target region of tissue.

In some examples, the composite metric may be associated with spectral power characteristics indicative of Beta waves. For example, a higher composite metric may be indicative of larger amplitudes of the spectral power for frequencies indicative of Beta waves and further indicate that the electrode is closer to the originating source of the Beta waves than an electrode with a lower composite metric. In other examples in which the system or clinician may desire to avoid stimulating these target tissues with strong signals, the system may select the electrode or electrodes with the lowest composite metric for stimulation.

In some examples, the system may select, based on at least one composite metric, at least one electrode that is closer to the target region of tissue to stimulate the target region of tissue. For example, after determining a plurality of composite metrics of a plurality of electrodes, the system may rank the composite metrics by magnitude. The system may then select the electrode with the highest composite metric, which may be indicative of the electrode being closest to the originating source of brain signals (e.g., Beta waves, LFPs, etc.). Additionally or alternatively, the system may present this information to a clinician to enable the clinician to review the composite metrics of the respective plurality of electrodes. The clinician may then select at least one electrode with an appropriate composite metric (e.g., the composite metric with the largest magnitude) for subsequent sensing and/or stimulation therapy.

A medical lead may carry the plurality of electrodes for sensing electrical signals and/or delivering electrical stimulation. For the sake of simplicity, the medical lead described in the examples herein may be generally cylindrical in shape so that electrodes disposed thereon may have an axial position along the length of the medical lead and a circumferential position around the perimeter of the lead. However, it should be understood that the techniques of this disclosure may be applied to a medical lead with any shape (e.g., the shape of a paddle) suitable for sensing electrical signals and/or delivering electrical stimulation.

In some examples, the medical lead may have electrodes (e.g., ring electrodes, electrodes that only reside around a limited portion of the perimeter of the lead, etc.) disposed at different axial positions along the length of the lead. For example, the medical lead may have electrodes at the same circumferential position around the perimeter of the lead and different axial positions along the length of the lead. In other examples, the medical lead may have electrodes at different circumferential positions around the perimeter of the lead and at the same axial position along the length of the lead (e.g., on the same level of the lead). In yet other examples, the system may group electrodes together as one polarity for use with another electrode(s) of another polarity. The system may perform such groupings in order to balance impedance between cathodes and anodes and improve sensing fidelity. In one example, to sense between a level with a ring electrode and a level with multiple smaller electrodes at different circumferential positions, the system may group those smaller electrodes at different circumferential positions to create a virtual ring electrode that may improve sensing between an actual ring electrode.

Sensing electrical signals between different electrodes, electrodes at different axial positions and at different circumferential positions, may provide valuable information about where certain electrical signals (e.g., signals in the Beta frequency band or Beta waves, alpha waves, gamma waves, theta waves, and high frequency oscillations (HFO)) are originating from within tissue. In this manner, the system (or a physician) may use this information to identify where a target region of tissue (e.g., the STN) is located and determine which electrode or electrodes (and/or other stimulation parameter values) should be used to deliver electrical stimulation therapy. In one example, the system may provide information representative of the sensed electrical signals (e.g., composite metrics of the corresponding electrodes) via a display to enable a clinician to program stimulation more effectively and in less time than using other trial-and-error approaches.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator (not shown in FIG. 1) configured to generate and deliver electrical stimulation therapy to the STN region of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to the STN within brain 28. DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

In the example shown in FIG. 1, IMD 16 may be implanted within a subcutaneous pocket in the pectoral region of patient 12. In other examples, IMB 16 may be implanted within other regions of patient 12, such as a subcutaneous pocket in the abdomen or buttocks of patient 12 or proximate the cranium of patient 12. Implanted lead extension 18 is coupled to IMB 16 via connector block 30 (also referred to as a header), that may include, for example, electrical electrodes that electrically couple to respective electrodes on lead extension 18. The electrical electrodes electrically couple the electrodes 24, 26 carried by leads 20 to IMB 16. Lead extension 18 traverses from the implant site of IMB 16 within a chest cavity of patient 12, along the neck of patient 12 and through the cranium of patient 12 to access brain 28. IMD 16 may be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, that may be selected based on many factors, such as the type of patient condition therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. In the case of Parkinson's disease, for example, leads 20 may be implanted to deliver electrical stimulation to regions within the STN, either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads. Furthermore, although leads 20 are illustrated as generally cylindrical in shape, they may be any shape suitable for sensing electrical signals and delivering electrical stimulation.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the perimeter (e.g., circumference) of the lead. The complex electrode array geometry may include multiple electrodes (e.g., partial ring or segmented electrodes), such as electrode levels 24B, 24C, 26B, and 26C that each include multiple individually programmable electrodes located at different circumferential positions. Although electrodes 24A, 24D, 26A, and 26D may be ring electrodes that each extend fully around the perimeter of the lead, any of these electrodes may be replaced by multiple electrodes located at different circumferential positions. By using electrodes disposed at different circumferential positions, electrical stimulation may be directed to a specific direction from leads 20 to enhance therapy efficacy and reduce possible adverse side effects from stimulating a large volume of tissue. As a further example, the electrodes may be pad electrodes, which may be carried on a paddle lead or a cylindrical lead.

As illustrated in the example of FIG. 1, the set of electrodes 24 of lead 20A may include electrodes 24A, 24B, 24C, and 24D, and the set of electrodes 26 of lead 20B may include electrodes 26A, 26B, 26C, and 26D. In some examples, each of electrodes 24 and 26 may be configured to independently deliver electrical stimulation.

In some examples, outer housing 34 of IMD 16 may include one or more stimulation and/or sensing electrodes. For example, housing 34 may comprise an electrically conductive material that is exposed to tissue of patient 12 when IMD 16 is implanted in patient 12, or an electrode may be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator (not shown in FIG. 1) of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off," stimulation is always on, and if cycling is "on," stimulation is cycled on and off) and, in the case of electrical stimulation pulses, pulse rate, pulse width, and other appropriate parameters such as duration or duty cycle. In addition, selection of electrodes 24, 26 and their respective polarities may further characterize a therapy parameter of a therapy program. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing circuitry that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the stimulation generator to target sites within brain 28 as well as sense brain signals within brain 28. However, IMD 16 may also use a separate set of sensing electrodes to sense the bioelectrical brain signals. In some examples, the sensing circuitry of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMB 16 as needed to provide or retrieve therapy information. Programmer 14 is an external computing device that the user, e.g., the clinician and/or patient 12, may use to communicate with IMB 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 14. A wireless adapter coupled to the computing device may enable secure communication between the computing device and IMB 16.

When programmer 14 is configured for use by the clinician, programmer 14 may be used to transmit programming information to IMB 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/ identification of therapy programs by providing a system for identifying potentially beneficial therapy parameter values. For example, during a programming session, the physician may select, in accordance with techniques described herein, an electrode combination for delivery of therapy to the patient. The physician may have the option to create several therapy programs. Some programs may have the same electrode combination (but different values of at least one other therapy parameter). The physician may select an efficacious therapy program (e.g., based on a ranking of composite metrics of the plurality of electrodes). For example, the clinician may select a therapy program based on a list of the composite metrics of the electrodes displayed on external programmer 14 to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques that may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment. In another example, a clinician in an operating room may obtain acute recordings during lead placement and before coupling the lead with an IMD. In this example, an external device (e.g., an external electrophysiology system) may couple to the medical lead in order to obtain sensed electrical signals.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 and electrode combinations for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, that may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In accordance with one or more techniques of this disclosure, and as discussed in further detail below, in some examples, medical leads 20 may be offset, or set a distance, from a signal source (e.g., Beta waves may be largely localized within the dorsal STN) in patient tissue (e.g., where the signal source could be within the STN of the left and/or right hemisphere). If a medical lead 20 is placed within or having a common axis with a signal source, the system may not distinguish the direction a signal is coming from. For example, the signals sensed by respective electrodes of medical leads 20 may be similar to each other because of the proximity of the signal source. For example, if a medical lead 20 is disposed at the origin of a signal source, any signal emanating from the signal source may appear to be around the medical lead as opposed to appearing to be located at only one circumferential direction to the medical lead. In this situation, any of the electrode combinations may be selected for delivery of stimulation. However, a clinician may implant a medical lead to be offset from a target tissue location in order to target that target tissue location and prevent damage to that target tissue location that could occur by implantation of the lead. Information representative of signal magnitude over frequency (e.g., spectral density) between an electrode combination (e.g., bipolar review) may be displayed for a clinician who may be determining stimulation therapy for the patient. Bipolar sensing generally describes sensing between electrodes on the same lead. Monopolar sensing generally describes sensing between an electrode on a lead and a remote electrode (e.g., an electrode or electrodes located a sufficient distance from the desired sensing location). In some examples, the remote electrode may be on the same lead, a different lead, the housing of the IMD, and the like. In any case, monopolar sensing generally records electrical signals more prevalent around a desired electrode, whereas bipolar sensing senses electrical activity between two relatively close electrodes.

In another example, medical lead 20 may be implanted directly at the target tissue (e.g., in a region with the strongest beta oscillation or largest amplitude of a target frequency). In another example, medical lead 20 may be implanted based purely on anatomy alone (e.g., placed in the STN). In either of these examples, due to various uncertainties associated with the lead placement procedure, the location of the medical lead may not be the same as the region generating the maximal signal source, resulting in an offset between the target anatomy and the lead location. However, it is not necessary for medical lead 20 to be offset from the target anatomy as a lead placed at the target tissue that generates the strongest signal may provide effective stimulation therapy. A clinician may choose to implant medical lead 20 offset from target tissue or directly at or within the target tissue that generates the strongest signal.

When using medical leads with larger number of electrodes, the time necessary for a review by a clinician grows. Further, the exploration and programming time required for directional stimulation across multiple combinations of electrodes increases as well. To reduce the time required of the patient and the clinician, in some examples, a representation of signal strength sensed by at least one electrode may be displayed to the clinician. The clinician may then select, or the system may automatically select, at least one electrode having greater signal strength (e.g., showing larger or the largest Beta wave signal strength, gamma wave signal strength, alpha wave signal strength, or any frequency of a desired signal). As described herein, the electrode having the greater signal strength as compared to other electrodes may be the electrode with the highest composite metric.

Therapy system 10 includes processing circuitry (not shown in FIG. 1) configured to perform techniques in accordance with this disclosure. Processing circuitry may be included in an external system (e.g., a peripheral device) or an internal system (e.g., IMD 16). The processing circuitry may be configured to determine, for each respective electrode combination of a plurality of electrode combinations, a respective metric based on a sensed electrical signal from the respective electrode combination. An electrode combination may be two or more electrodes (e.g., an anode, a cathode, etc.) across which electrical signals are sensed. For example, a first electrode combination may be 24B-24C, and a second electrode combination may be 24A-24D. Thus, in this example, the processing circuitry may be configured to determine a metric for the first electrode combination based on the electrical signals sensed by the first electrode combination and a metric for the second electrode combination based on electrical signals sensed by the second electrode combination. The metric may use any unit of measurement appropriate for quantifying sensed electrical signals. For example, the metric may be in units of volts. Alternatively, the metric may not use a standard unit, and the metrics for the electrode combinations may be compared with each other for an indication of their relative differences.

The processing circuitry may further determine, for each respective electrode of a plurality of electrodes, a subset of electrode combinations of the plurality of electrode combinations. Each electrode combination of the subset of electrode combinations may include the respective electrode, wherein the subset of electrode combinations includes at least two electrode combinations. For example, a subset of electrode combinations may be 24A-24B, 24A-24C, and 24A-24D, where 24A is the electrode included (e.g., common electrode) in each electrode combination of the subset of electrode combinations.

The processing circuitry may further determine, for each respective electrode of the plurality of electrodes, a respective composite metric based on the respective metrics of the subset of electrode combinations. For example, the processing circuitry may determine a composite metric for 24A by determining an average of the metrics for 24A-24B, 24A-24C, and 24A-24D. The average determined by the processing circuitry may be a mean, median, mode, weighted average, or any other mathematical operation or algorithm for determining a value representative of the metrics for the subset of electrode combinations. The processing circuitry may then determine a composite metric for the remaining electrodes (e.g., 24B, 24C, 24D, etc.) in a similar fashion.

After determining the respective composite metrics of the plurality of electrodes, the processing circuitry may select, based on the respective composite metrics of the plurality of electrodes, at least one electrode for at least one of sensing electrical signals or delivering electrical stimulation. For example, if 24A has the highest composite metric, the processing circuitry may select 24A for sensing electrical signals and/or electrical stimulation.

In some examples, electrode combinations in which a specific electrode is included may comprise electrodes located at different axial positions along the length of medical lead 20 and located at the same circumferential position around the perimeter of medical lead 20. Determining a composite metric for the electrodes located at different axial positions may provide insight for the clinician as to the electrode at an axial position that may provide efficacious stimulation therapy. For example, a first electrode with the highest composite metric indicative of the strongest sensed signal strength may indicate that the first electrode is closest to an axial location along the length of medical lead 20 for which target tissue is located.

In some examples, a subset of electrode combinations in which a specific electrode is included (e.g., a common electrode) may include electrodes located at different circumferential positions around the perimeter of medical lead 20 and located at the same axial position along the length of medical lead 20. Determining a composite metric for the electrodes located at different circumferential positions may provide insight for the clinician as to the electrode at a circumferential position that may provide efficacious stimulation therapy. For example, a first electrode with the highest composite metric indicative of the strongest sensed signal strength may indicate that the first electrode is closest to a circumferential location around the perimeter of medical lead 20 for which target tissue is located. In any case, each of the electrode combinations in a subset of electrode combinations only need to include at least one common electrode so that a composite metric for the common electrode may be determined.

Since an electrode combination may be required to sense electrical signals and/or deliver electrical stimulation, determining two or more electrodes with composite metrics for sensing electrical signals and delivering electrical stimulation may be desirable. For example, a programming therapy may require selecting a first electrode with the highest composite metric and using the first electrode as a cathode. The programming therapy may further require selecting a second electrode with the second-highest composite metric and using the second electrode as an anode. The first electrode and the second electrode may be the two electrodes closest to the target tissue, and the electrode combination including the first electrode and the second electrode may transmit energy to produce an electric field in a direction between the first electrode and the second electrode that is toward the target tissue. An electrode combination closet to target tissue may be utilized to provide efficacious stimulation therapy. As such, the processing circuitry may be configured to determine the composite metrics of as many electrodes as necessary and select electrodes suitable for sensing electrical signals and/or delivering electrical stimulation based on the respective composite metrics.

Therapy system 10 may further include sensing circuitry (not shown in FIG. 1) configured to sense electrical signals from the plurality of electrode combinations, wherein each electrode of the plurality of electrode combinations is carried by a medical lead, and wherein the medical lead comprises electrodes at different positions on the medical lead. For example, a device (e.g., IMD 16, programmer 14, and/or another computing device) may include sensing circuitry configured to sense electrical signals from an electrode combination of a plurality of combinations of electrodes. As one example, IMD 16 may sense electrical signals (e.g., sub-microvolt LFPs) from combinations of electrodes 24 and/or electrodes 26.

These sensed electrical signals for the particular patient from combinations of electrodes 24 and/or electrodes 26 may be represented on a display or user interface (not shown in FIG. 1) at programmer 14, and/or another computing device. A clinician may select an electrode combination to provide stimulation therapy based on sensed signals from a plurality of electrode combinations. For instance, a clinician may select an electrode combination using one or more of electrodes 24, electrodes 26, and/or an electrode of IMD 16 (e.g., a case electrode or can electrode). In some examples, each respective representation of electrical signals of the plurality of representations of electrical signals is associated with respective composite metrics of the plurality of electrodes.

IMD 16 may be configured to deliver electrical stimulation to the patient via the clinician or system selected electrode combination. As one example, where the processing circuitry selects the electrode, the IMD may deliver electrical stimulation to the patient via the selected electrode combination. As yet another example, the clinician may input the selected electrode combination to programmer 14 such that programmer 14 automatically selects a therapy and configures IMD 16 to deliver electrical stimulation to the patient via the selected electrode combination. As yet another example, the clinician may use a computing device to select an electrode combination that may be communicated to programmer 14 that may configure IMD 16 to deliver electrical stimulation to the patient via the clinician-selected electrode combination.

Figure 2:
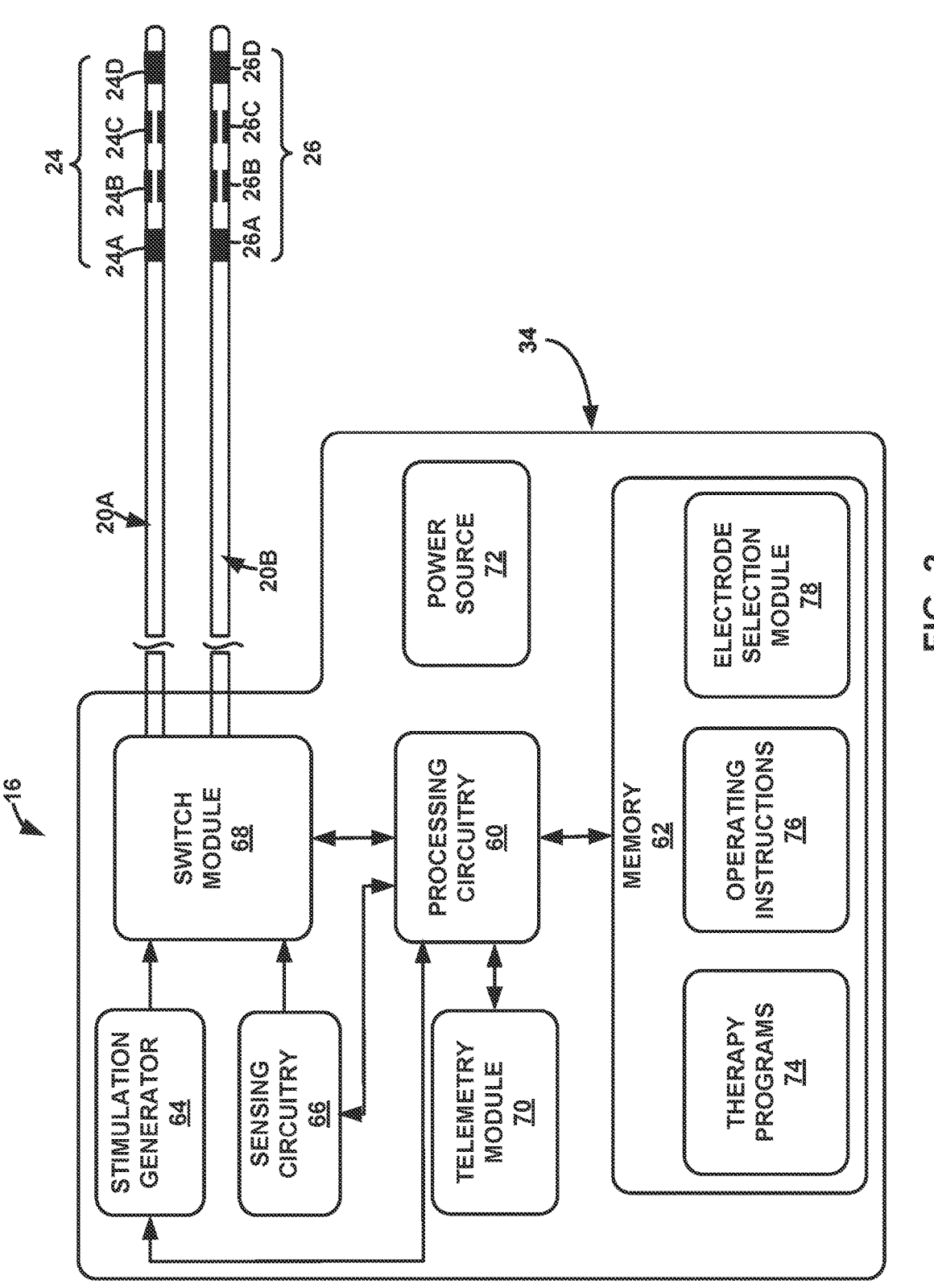
FIG. 2 is functional block diagram illustrating components of an example medical device.

FIG. 2 is functional block diagram illustrating components of an example IMD 16. In the example shown in FIG. 2, IMD 16 includes processing circuitry 60, memory 62, stimulation generator 64, sensing circuitry 66, switch module 68, telemetry module 70, and power source 72. Memory 62, as well as other memories described herein, may include any volatile or non-volatile media, such as a random-access memory (RAM), read only memory (ROM), non-volatile RAM (NVRAM), electrically erasable programmable ROM (EEPROM), flash memory, and the like. Memory 62 may store computer-readable instructions that, when executed by processing circuitry 60, cause IMD 16 to perform various functions described herein.

In the example shown in FIG. 2, memory 62 may store therapy programs 74, operating instructions 76, and electrode selection module 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processing circuitry 60 and may include instructions for monitoring brain signals within one or more brain regions via electrodes 24, 26 and delivering electrical stimulation therapy to patient 12. As discussed in further detail below and in accordance with one or more techniques of this disclosure, in some examples, memory 62 may store electrode selection module 78, that may include instructions that are executable by processing circuitry 60 to select one or more electrodes to sense electrical signals and/or deliver electrical stimulation. For instance, electrode selection module 78 may be executable by processing circuitry 60 to select one or more electrode combinations of electrodes 24 and/or electrodes 26 to sense physiological signals and/or deliver electrical stimulation in accordance with the techniques of FIG. 4.

Stimulation generator 64, under the control of processing circuitry 60, generates stimulation signals for delivery to patient 12 via selected combinations of electrodes 24, 26. In some examples, stimulation generator 64 generates and delivers stimulation signals to one or more target regions of brain 28 (FIG. 1), via a selected electrode combination from electrodes 24, 26, based on one or more stored therapy programs 74. In some examples, therapy programs 74 are determined (e.g., automatically, manually by a user, or semi-automatically based on user input) by external programmer 14 and/or an external computer and transferred to IMD 16 and stored in memory 62. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processing circuitry described in this disclosure, including processing circuitry 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processing circuitry 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A-24D, and the set of electrodes 26 of lead 20B includes electrodes 26A-26D. Processing circuitry 60 may control switch module 68 to apply the stimulation signals generated by stimulation generator 64 to a selected electrode combination from electrodes 24 and/or electrodes 26. In particular, switch module 68 may couple stimulation signals to selected conductors within leads 20, that, in turn, deliver the stimulation signals across selected electrodes 24 and/or electrodes 26. Switch module 68 may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. Hence, stimulation generator 64 is coupled to electrodes 24 and/or electrodes 26 via switch module 68 and conductors within leads 20. In some examples, however, IMD 16 does not include switch module 68. For instance, in some examples, IMD 16 may include individual voltage or current sources coupled to each electrode (i.e., a separate voltage and/or current source for each of electrodes 24 and/or electrodes 26).

As discussed above, processing circuitry 60 may control switch module 68 to apply the stimulation signals generated by stimulation generator 64, or sense electrical signals by sensing circuitry 66, to a selected electrode combination of electrodes 24 and/or electrodes 26. In some examples, the selected electrode combination of electrodes 24 and/or electrodes 26 may be unipolar. For instance, a unipolar selected combination may include one electrode of either electrodes 24 or electrodes 26 in combination with an electrode on the housing of IMD 16 (i.e., case or can), where one is an anode and the other is a cathode. In some examples, the selected electrode combination of electrodes 24 and/or electrodes 26 may be bipolar. As one example, a bipolar selected combination may include two electrodes from electrodes 24, where one is an anode and the other is a cathode. As another example, a bipolar selected combination may include two electrodes from electrodes 26, where one is an anode and the other is a cathode. As another example, a bipolar selected combination may include an electrode from electrodes 24 and an electrode from electrodes 26, where one is an anode and the other is a cathode. In some examples, the selected electrode combination of electrodes 24 and/or electrodes 26 may be multipolar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing circuitry 66, under the control of processing circuitry 60, is configured to sense bioelectrical brain signals of patient 12 via a selected subset of electrode combinations with one or more electrodes 24 and/or electrodes 26 and at least a portion of a conductive outer housing 34 of IMD 16, an electrode on an outer housing of IMD 16 or another reference. Processing circuitry 60 may control switch module 68 to electrically connect sensing circuitry 66 to selected electrodes 24 and/or electrodes 26. In this way, sensing circuitry 66 may selectively sense bioelectrical brain signals with different combinations of electrodes 24 and/or electrodes 26 (and/or a reference other than an electrode of electrodes 24 and/or electrodes 26).

Although sensing circuitry 66 is incorporated into a common housing 34 with stimulation generator 64 and processing circuitry 60 in FIG. 2, in other examples, sensing circuitry 66 is in a separate outer housing from outer housing 34 of IMD 16 and communicates with processing circuitry 60 via wired or wireless communication techniques.

Telemetry module 70 is configured to support wireless communication between IMD 16 and an external programmer 14 or another computing device under the control of processing circuitry 60. Processing circuitry 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62, as discussed above. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energyscavenging device to trickle charge a rechargeable battery. In other examples, traditional batteries may be used for a limited period of time.

Figure 3:
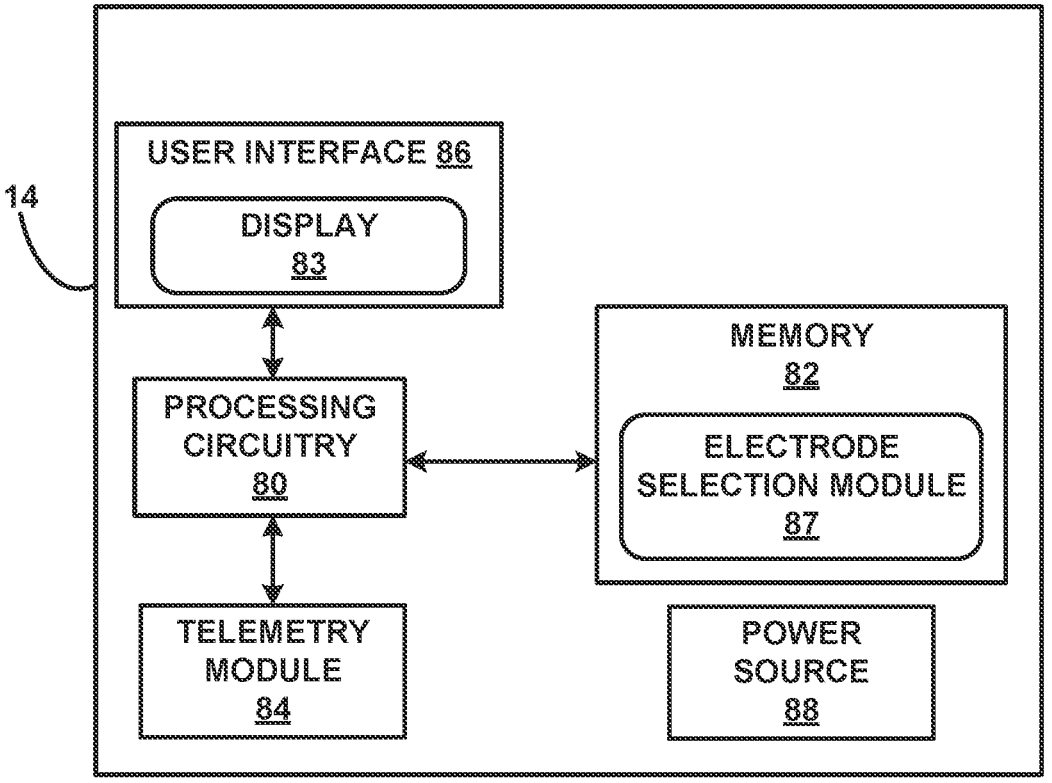
FIG. 3 is a functional block diagram illustrating components of an example medical device programmer.

FIG. 3 is a functional block diagram illustrating components of an example medical device programmer 14 (FIG. 1). In the example of FIG. 3, programmer 14 includes processing circuitry 80, memory 82, telemetry module 84, user interface 86 with display 83, and power source 88. Processing circuitry 80 controls user interface 86 and telemetry module 84 and stores and retrieves information and instructions to and from memory 82. Programmer 14 may be configured for use as a clinician programmer or a patient programmer. Processing circuitry 80 may comprise any combination of one or more processors including one or more microprocessors, DSPs, ASICs, FPGAs, or other equivalent integrated or discrete logic circuitry. Accordingly, processing circuitry 80 may include any suitable structure, whether in hardware, software, firmware, or any combination thereof, to perform the functions ascribed herein to processing circuitry 80.

A user, such as a clinician or patient 12, may interact with programmer 14 through user interface 86. User interface 86 includes a display 83, such as an LCD or LED display or other type of screen, with which processing circuitry 80 may present information related to the therapy (e.g., electrode combinations and associated therapeutic windows) and sensed electrical signals. In addition, user interface 86 may include an input mechanism to receive input from the user. The input mechanisms may include, for example, any one or more of buttons, a keypad (e.g., an alphanumeric keypad), a peripheral pointing device, a touch screen for display 83, or another input mechanism that allows the user to navigate through user interfaces presented by processing circuitry 80 of programmer 14 and provide input. In other examples, user interface 86 also includes audio circuitry for providing audible notifications, instructions or other sounds to patient 12, receiving voice commands from patient 12, or both. Programmer 14 may be configured as a patient programmer or a clinician programmer by providing different user interface elements. For example, the patient programmer user interface may include fewer user adjustable settings than available via the clinician programmer user interface such that the clinician programmer enables greater adjustment of sensing and/or stimulation via IMD 16.

Memory 82 may include instructions for operating user interface 86 and telemetry module 84, and for managing power source 88. In the example shown in FIG. 3, memory 82 also stores electrode selection module 87. Electrode selection module 87 may be similar to electrode selection module 78 of FIG. 2. As discussed in further detail below and in accordance with one or more techniques of this disclosure, in some examples, memory 82 of programmer 14 may store electrode selection module 87, that may include instructions that are executable by processing circuitry 80 to select one or more electrodes, and electrode combinations to sense electrical signals and/or deliver electrical stimulation. For instance, electrode selection module 87 may be executable by processing circuitry 80 to select one or more of electrodes and electrode combinations to sense electrical signals in accordance with the techniques described below. In some examples, memory 82 may include additional information, such as information similar or the same as therapy programs 74 and operating instructions 76 of IMD 16 in FIG. 12.

In some examples, patient 12, a clinician or another user may interact with user interface 86 of programmer 14 in other ways to manually select therapy programs, or combinations of electrodes (e.g., based on the composite metrics of the plurality of electrodes), generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information may alternatively or additionally be stored within memory 62 of IMD 16. Moreover, at least some of the functionality ascribed to processing circuitry 80 of programmer 14 may instead or additionally be ascribed to processing circuitry 60 of IMD as discussed below (and vice versa).

FIGS. 4A and 4B are conceptual diagrams of example leads 400 and 410, respectively, with respective electrodes carried by the lead. As shown in FIGS. 4A and 4B, leads 400 and 410 are example configurations that may be similar to leads 20 shown in FIG. 1. As shown in FIG. 4A, lead 400 includes four electrode levels 404 (includes levels 404A-404D) mounted at various lengths of lead housing 402. Lead 400 is inserted into through cranium 32 to a target position within brain 28.

Lead 400 is implanted within brain 28 at a location determined by the clinician to be near an anatomical region to be stimulated. Electrode levels 404A, 404B, 404C, and 404D (collectively, electrode levels 404) may be equally spaced along the axial length of lead housing 402 at different axial positions. Each electrode level 404 may have one, two, three, or more electrodes located at different circumferential positions around the perimeter of lead housing 402. As shown in FIG. 4A, electrode level 404A and 404D include a single respective ring electrode, and electrode levels 404B and 404C each include three electrodes at different circumferential positions around the perimeter of lead 400. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include one or more radiopaque stripes or other radiopaque orientation markers (not shown) along the outside of the lead housing. The radiopaque stripe corresponds to a certain circumferential location that allows lead 400 to the imaged when implanted in patient 12. Using the images of patient 12, the clinician can use the radiopaque stripe as a marker for the exact orientation of lead 400 within the brain of patient 12. Orientation of lead 400 may be needed to easily program the stimulation parameters by generating the correct electrode configuration to match the stimulation field defined by the clinician. In other examples, a marking mechanism other than a radiopaque stripe may be used to identify the orientation of lead 400. These marking mechanisms may include something similar to a tab, detent, or other structure on the outside of lead housing 402. In some examples, the clinician may note the position of markings along a lead wire during implantation to determine the orientation of lead 400 within patient 12.

FIG. 4B illustrates lead 410 that includes multiple electrodes at different respective circumferential positions around the perimeter of lead 410 at each of levels 414A-414D. Similar to lead 400, lead 410 is inserted through a burr hole in cranium 32 to a target location within brain 28. Lead 410 includes lead housing 412. Four electrode levels 414 (e.g., electrode levels 414A-414D) are located at the distal end of lead 410. Each electrode level 414 is evenly spaced from the adjacent electrode level(s) and includes two or more electrodes. In one example, each electrode level 414 includes three, four, or more electrodes distributed around the circumference of lead housing 412. Therefore, lead 410 includes electrodes 414. Each electrode may be substantially rectangular in shape. Alternatively, the individual electrodes may have alternative shapes, e.g., circular, oval, triangular, rounded rectangles, or the like.

In alternative examples, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 28 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other examples, leads 400 or 410 may be shaped differently than a cylinder. For example, the leads may include one or more curves to reach target anatomical regions of brain 28. In some examples, leads 400 or 410 may be similar to a flat paddle lead or a conformable lead shaped for patient 12. Also, in other examples, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by the user interface.

FIG. 5B shows electrode level 510 that includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

FIG. 5C shows electrode level 520 that includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

FIG. 5D shows electrode level 530 that includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other examples, up to ten or more electrodes may be included within an electrode level. In alternative examples, consecutive electrode levels of lead 20 may include a variety of electrode levels 500, 510, 520, and 530. For example, lead 20 (or any other lead described herein) may include electrode levels that alternate between electrode levels 510 and 530 depicted in FIGS. 5B and 5D. In this manner, various stimulation field shapes may be produced within brain 28 of patient 112. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted at tissues needing certain shaped stimulation fields.

Figure 6:
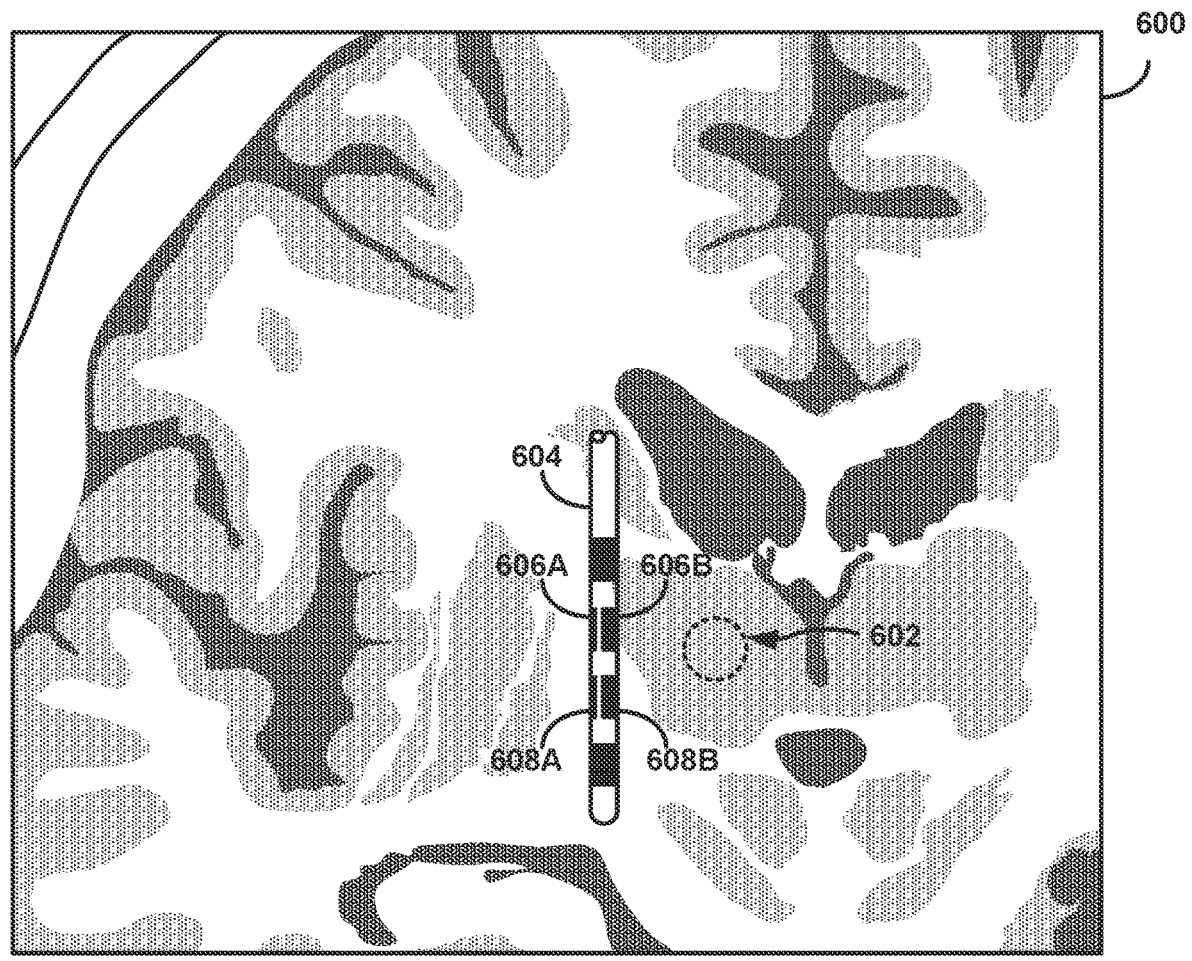
FIG. 6 is a coronal view of example tissue with a lead placed with respect to a target location within tissue.

FIG. 6 is a coronal view of example tissue with a lead 604 placed offset with respect to a target location within tissue. As shown in FIG. 6, a representation of anatomical regions of brain 28 is displayed by coronal view 600. Coronal view 600 is a front-back vertical section of brain 28. Coronal view 600 may be an actual image of brain 28 produced with magnetic resonance imaging (MRI), computed tomography (CT), or another imaging modality. Coronal view 600 may be an illustration of the location of a lead with respect to a target tissue from which electrical signals originate (e.g., LFP signals). In some examples, coronal view 600 may be presented by programmer 14, for example on display 83, or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 28. Differently shaded portions of coronal view 600 indicate varying densities of tissue within brain 28. Darker portions indicate less dense tissue. For example, the darkest portion of coronal view 600 is indicative of spaces within brain 28 that contain cerebral spinal fluid (CSF). White portions of brain 28 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 6, lead 604 may be a lead icon that represents an actual lead implanted within patient 12. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located on the backside of lead 604. When electrical signals, such as LFP signals originate from target tissue 602, the largest amplitude and power of the signal will likely be sensed by the electrode or electrodes closest to target tissue 602. In this example, a sensing electrode 606A may be sensing a larger amplitude electrical signal from target tissue 602 than any other electrode on lead 604 based on the composite metrics for sensing electrode 606A and the other electrodes (e.g., 606B, 608A, and 608B). In some examples, another electrode may be sensing the highest amplitude of electrical signals from target tissue 602. For example, if lead 604 moves with respect to tissue, a different electrode, such as electrode 606B (for lead rotation) or electrode 608B (for longitudinal lead movement), may be sensing electrical signals with the largest amplitude.

Leads, such as lead 604, may be offset from a signal-source, such as target tissue 602. As stated above, lead 604 is offset from the signal-source so that electrodes 606A, 606B, 608A and 608B are all implanted at a distance from the signal-source. This offset may enable identification of the direction of the signal-source because different electrodes are different distances from the signal-source due to their respective locations along the lead. In examples of the present disclosure, target tissue 602 may be within the dorsal STN.

Figure 7:
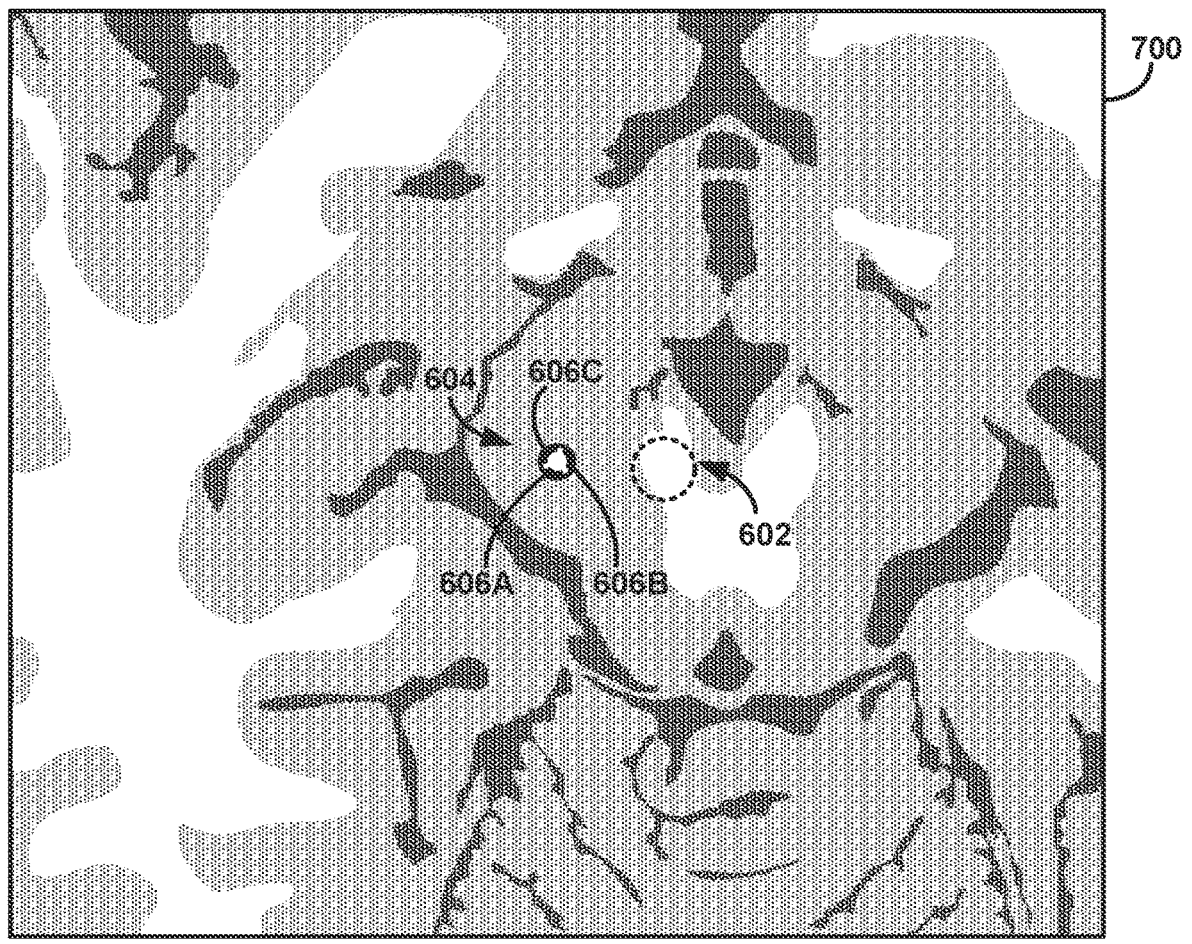
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude when compared to other electrodes. Although FIGS. 6 and 7 discuss electrical signals that may originate in tissue, the same spatial origin may be used when sensing electrical signals evoked from delivered stimulation or sensing delivered stimulation itself for determining lead movement.

Figure 8:
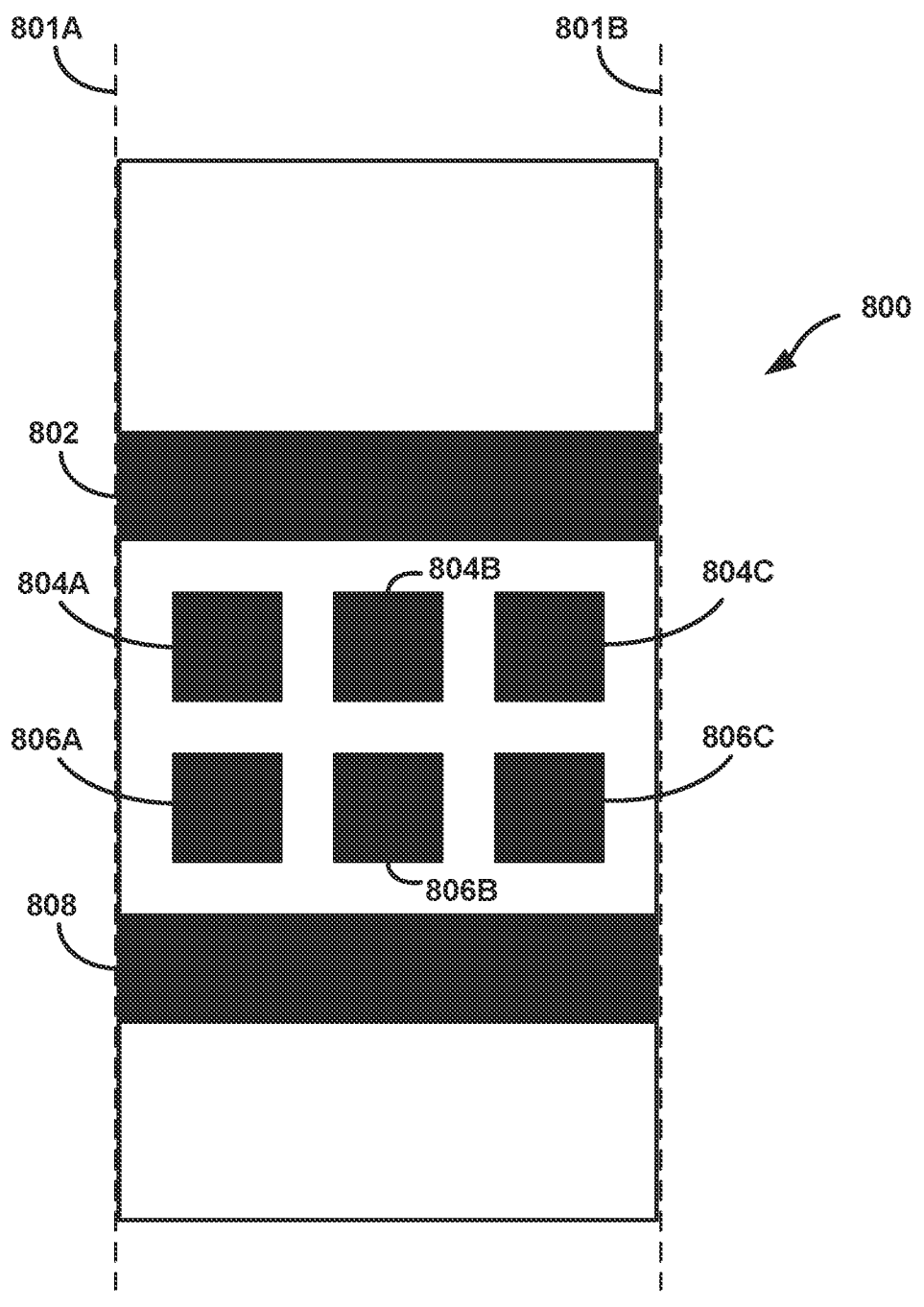
FIG. 8 is a conceptual diagram of example electrodes selectable for electrode combinations and subsets of electrode combinations, in accordance with one or more techniques of this disclosure.

FIG. 8 is a conceptual diagram illustrating example electrodes that are selectable in various combinations in order to form different electrode combinations that may be a part of the same or different subsets of electrode combinations, in accordance with one or more techniques of this disclosure. As shown in FIG. 8, medical lead 800 is represented as an unwrapped view to show all electrodes in a two dimensional view. Medical lead may be similar to lead 400 of FIG. 4A, for example. Medical lead 800 may take the form of a cylinder or other three dimensional structure if the unwrapped view were curved such that dashed lines 801A and 801B meet together.

Medical lead 800 carries electrodes 802, 804A, 804B, 804C, 806A, 806B, 806C, and 808. Electrodes 802 and 808 may be referred to as ring electrodes disposed about the perimeter of the lead, and electrodes 804A, 804B, 804C, 806A, 806B, and 806C may be referred to as segmented electrode or electrodes located at different positions around the perimeter of the lead. Two or more electrodes may be selected as part of a single electrode combination. As already described, processing circuitry 80 is configured to determine, for each electrode combination of a plurality of electrode combinations, a respective metric based on a sensed electrical signal from the respective electrode combination. With respect to FIG. 8, example electrode combinations may include, but are not limited to, 804A-804B, 804A-804C, 804A-806A, 804A-806B, 804A-806C, 804B-804C, and the like. Thus, processing circuitry may determine, based on the sensed electrical signal from the respective electrode combination (e.g., 804A-804B), the respective metric (e.g., in units of volts) for at least some of the possible electrode combinations.

Processing circuitry 80 is further configured to determine, for each electrode of a plurality of electrodes (e.g., 802, 804A, 804B, 804C, 806A, 806B, 806C, 808, etc.) a subset of electrode combinations of the plurality of electrode combinations. Each electrode combination of the subset of electrode combinations may include the respective electrode (e.g., the common electrode). For example, with respect to FIG. 8, if 804A is the common electrode, then the subset of electrode combinations for 804A may include two or more electrode combinations of the electrode combinations 804A-804B, 804A-804C, 804A-806A, 804A-806B, 804A-806C. In one example, the subset of electrode combinations for common electrode 804A may only include two electrode combinations on the same level, such as electrode combinations 804A-804B and 804A-804C. However, the subset of electrode combinations may include electrodes from different levels (e.g., electrode combination 804A-806A or additional levels). Electrodes of different sizes may also be used. In some examples, the subsets of electrode combinations for different common electrodes may be entirely different or have one or more of the same electrode combinations in different subsets. Processing circuitry 80 may determine a subset of electrode combinations for not only 804A, but also each of the other electrodes of the plurality of electrodes (e.g., 802, 804B, 804C, 806A, 806B, 806C, and/or 808). Thus, it should be understood that the above example with respect to electrode 804A may be applied to at least two electrodes and up to all of the electrodes carried by medical lead 800.

Processing circuitry 80 is further configured to determine for each electrode of the plurality of electrodes, a respective composite metric based on the respective metrics of the subset of electrode combinations. For example, if 804A is the common electrode and the subset of electrode combinations for 804A includes the electrode combinations 804A-804B and 804A-804C, then processing circuitry 80 may determine a composite metric for the common electrode 804A by averaging the metrics for each of the electrode combinations in the subset of electrode combinations for 804A. The average determined by processing circuitry 80 may be a mean, median, mode, weighted average, or any other mathematical operation or algorithm for determining a value representative of the metrics for the subset of electrode combinations. In some examples, processing circuitry 80 may reduce the weighting of electrode combinations that include electrodes of a further distance from the common electrode than other electrode combinations. The processing circuitry may then determine a composite metric for one or more of the remaining electrodes (e.g., 802, 804B, 804C, 806A, 806B, 806C, 808, etc.) in a similar fashion. Processing circuitry 80 may also be configured to select, based on the respective composite metrics of the plurality of electrodes, at least one electrode for at least one of sensing electrical signals or delivering electrical stimulation. For example, if, after determining the composite metrics of the plurality of electrodes, processing circuitry determines that electrodes 806A and 806B have the highest composite metric and the second-highest composite metric, respectively, processing circuitry 80 may select electrodes 806A and 806B to form electrode combination 806A-808. Processing circuitry 80 may then use electrode combination 806A-806B to deliver stimulation therapy.

Figure 9:
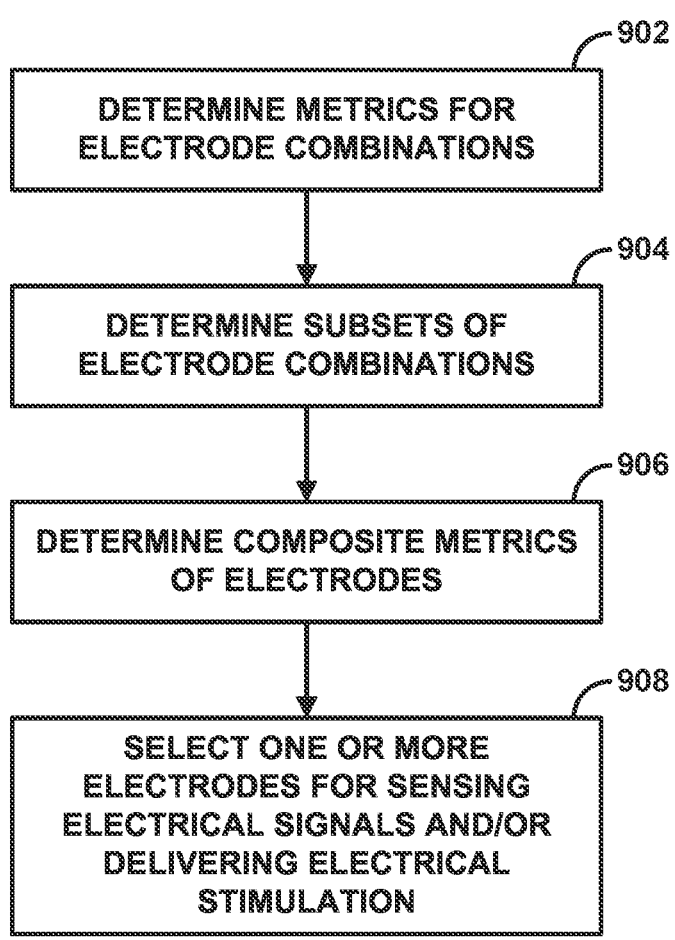
FIG. 9 is a flow diagram of an example technique for selecting an electrode, in accordance with one or more techniques of this disclosure.

FIG. 9 is a flow diagram of an example technique for selecting an electrode of a plurality of electrodes based on respective composite metrics of the plurality of electrodes, in accordance with one or more techniques of this disclosure. Processing circuitry 80 of programmer 14 will be described for the example of FIG. 9, but any devices herein, or combinations of devices, may perform similar techniques of FIG. 9.

In the example of FIG. 9, processing circuitry 80 is configured to determine, for each respective electrode combination of a plurality of electrode combinations, a respective metric based on a sensed electrical signal from the respective electrode combination (902). The sensed electrical signals may be LFPs, spectral power of a Beta frequency band within the sensed LFPs, a different type of electrical signal, an evoked signal from a delivered stimulus, or any other appropriate electrical signal generated by the brain.

Processing circuitry 80 is further configured to determine, for each respective (e.g., common) electrode of a plurality of electrodes, a subset of electrode combinations of the plurality of electrode combinations (904). In this manner, each electrode combination of one subset of electrode combinations include one electrode in common (e.g., common electrode). The subset of electrode combinations may include at least two electrode combinations. Processing circuitry 80 may determine a subset of electrode combinations for each electrode carried by a lead, or only some of the electrodes carried by the lead. In some examples, processing circuitry 80 may perform aspects of FIG. 9 in different orders or with one or more alternative features. For example, processing circuitry 80 may determine the subsets of electrode combinations (904) prior to determining the metrics for each electrode combination (902).

Processing circuitry 80 is also further configured to determine, for each respective electrode of the plurality of electrodes, a respective composite metric based on the respective metrics of the subset of electrode combinations for that respective electrode (906). For example, processing circuitry 80 may average the metrics of the subset of electrode combination to determine the composite metric for the common electrode of the respective subset of electrode combination.

Processing circuitry 80 may be further configured to select, based on the respective composite metrics of the plurality of electrodes, at least one electrode for at least one of sensing electrical signals or delivering electrical stimulation (908). For example, processing circuitry 80 may select the electrode with the highest composite metric for delivering electrical stimulation, such as the cathode of an electrode combination with one or more additional electrodes. Processing circuitry 80 may perform the process of FIG. 8.

In some examples, IMD 16 may include sensing circuitry 66. Sensing circuitry 66 may be configured to sense electrical signals from a subset of electrode combinations, such as waveform amplitudes. IMD 16 may transmit the sensed electrical signals (or representative data thereof) to programmer 14 for determination of the composite metrics and programming as described herein.

In some examples, processing circuitry 60 may rank the plurality of electrodes based on their corresponding composite metrics and select, from the plurality of electrodes and based on the ranking, one or more of the electrodes for delivery of electrical stimulation. For example, with respect to FIG. 7, processing circuitry may identify electrode 606B as the electrode closest to the target region 602 of tissue because it had the highest composite metric of the ranking of composite metrics of the plurality of electrodes (e.g., 606A, 606B, 606C, 608A, 608B, and 608C). Processing circuitry 66 may set the selected electrode with the highest composite metric (e.g., 606A) as a cathode and one or more other electrodes with lower composite metrics as anodes of the electrode combination for delivery of electrical stimulation. For example, processing circuitry 66 may select the electrode with the second highest composite metric as the anode to deliver stimulation with the electrodes closest to the target region of tissue. Processing circuitry 66 may then control delivery of electrical stimulation to use these selected electrodes.

In another example, the clinician may select (e.g., based on the ranking of composite metrics) an electrode combination. For example, if two or more composite metrics are identical, similar, or otherwise suitable for sensing electrical signals and/or delivering electrical stimulation, the clinician may want to store the electrodes associated with those composite metrics to assist in the selection of the stimulation electrodes when viewed with all the electrode information at the end of the electrode selection process.

In another example, programmer 14 may automatically select the electrode or electrodes based upon the composite metrics of the plurality of electrodes. The automatic selection may be based upon the highest composite metric. In another example, programmer 14 may identify electrodes associated with the lowest composite metric. For example, the lowest composite metric may be indicative of white-matter tracts in the brain which tend to have very weak signals compared to the surrounding gray matter. In this manner, the electrodes associated with the lower composite metrics may be selected to target stimulation to these white-matter tracks to treat conditions associated with dysfunction of these white-matter tracks.

Figure 10:
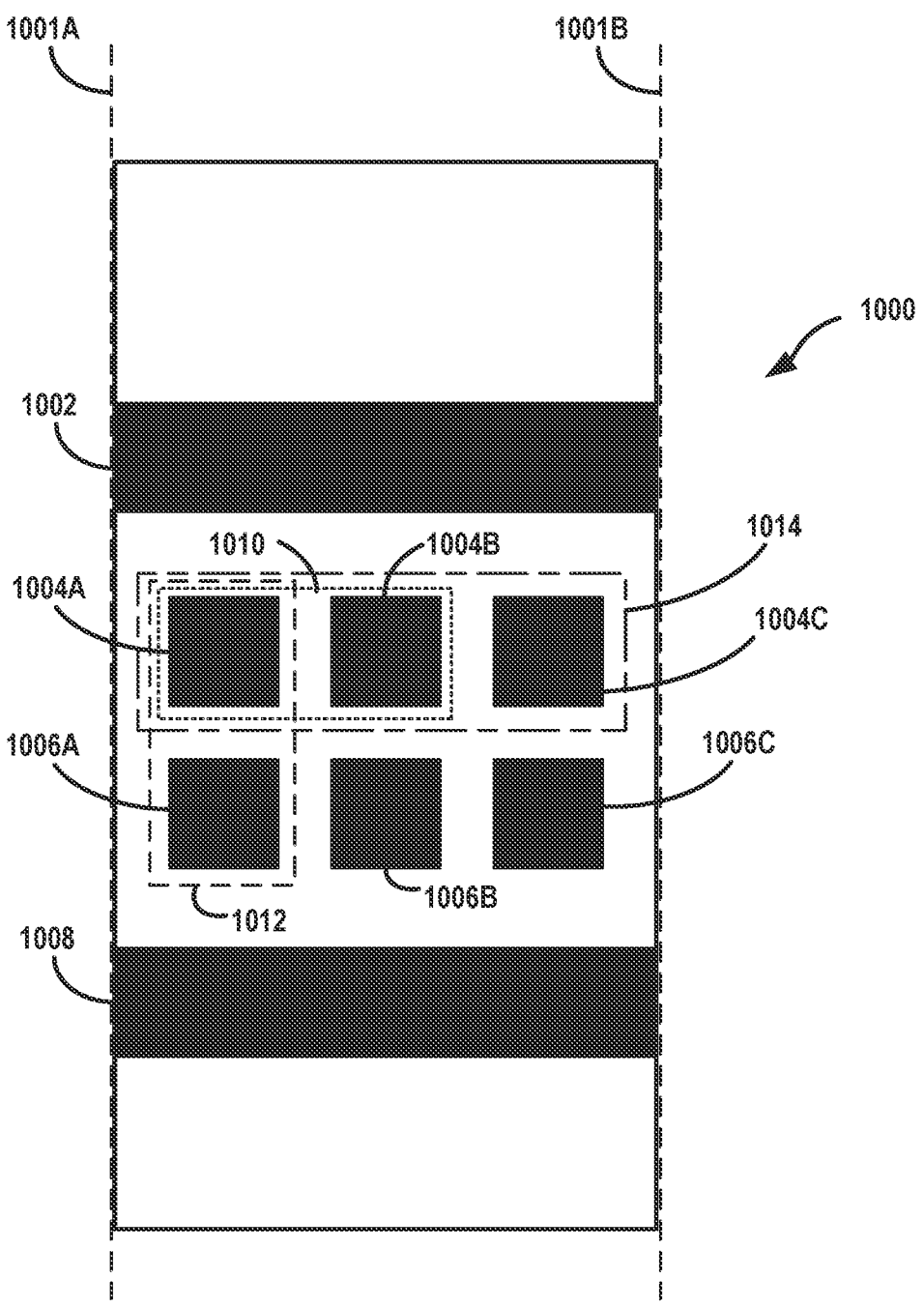
FIG. 10 is conceptual diagram of example subsets of electrode combinations to determine composite metrics of electrodes, in accordance with one or more techniques of this disclosure.

FIG. 10 is conceptual diagram of various types of electrode combinations and subsets of electrode combinations that may be weighed to determine composite metrics of electrodes, in accordance with one or more techniques of this disclosure. As shown in FIG. 10, medical lead 1000 is represented as an unwrapped view to show all electrodes in a two-dimensional view. Medical lead may be similar to lead 400 of FIG. 4A and lead 800 of FIG. 8, for example. Medical lead 1000 may take the form of a cylinder or other three dimensional structure if the unwrapped view were curved such that dashed lines 1001A and 1001B meet together.

Like with lead 800, processing circuitry 80 may be configured to determine, for each electrode, a respective composite metric based on the respective metrics of the subset of electrode combinations. For example, if 1004A of lead 1000 is the common electrode, then processing circuitry 80 may determine a composite metric for the common electrode 1004A by averaging the metrics for each of the electrode combinations in the subset of electrode combinations for 1004A. The average determined by processing circuitry 80 may be a mean, median, mode, weighted average, or any other mathematical operation or algorithm for determining a value representative of the metrics for the subset of electrode combinations.

The subset of electrode combinations for 1004A may include various types of electrode combinations. These types of electrode combinations may include horizontal electrode combinations 1010 (e.g., 1004A-1004B, 1004A-1004C, etc.), vertical electrode combinations 1012 (e.g., 1004A-1006A), ring electrode combinations 1014 (e.g., 1004ABC (e.g., by grouping 1004A, 1004B, and 1004C to create virtual ring electrode 1004ABC)-1002, 1004ABC-1006ABC, 1004ABC-1008, etc.) diagonal electrode combinations (e.g., 1004A-1006B, 1004A-1006C, etc.), and the like.

In some examples, processing circuitry 80 may determine a composite metric for the common electrode 1004A by calculating a weighted average of the metrics for each of the electrode combinations in the subset of electrode combinations for 1004A. Processing circuitry 80 may multiply the respective average of each type of electrode combinations by a respective weight to calculate the weighted average of the metrics. For example, may multiply the average of horizontal electrode combinations 1010 including 1004A (e.g., 1004A-1004B, 1004A-1004C, etc.) by a weight of 0.5, the average of vertical electrode combinations 1012 including 1004A (e.g., 1004A-1006A) by a weight of 0.25, and the ring electrode combinations 1014 (e.g., 1004ABC-1002, 1004ABC-1006ABC, 1004ABC-1008, etc.) by a weight of 0.25. Processing circuitry 80 may then add the weighted averages of horizontal electrode combinations 1010, vertical electrode combinations 1012, and ring electrode combinations 1014 to determine the composite metric of the common electrode 1004A. Processing circuitry 80 may determine the composite metric for each electrode of the plurality of electrodes of lead 1000 in a similar fashion. It should be understood that the respective weights processing circuitry 80 uses for the various types of electrode combinations to determine the weighted average may be any number or percentage (e.g., 0.1, 0.2, 5, 10, etc.).

Figure 11:
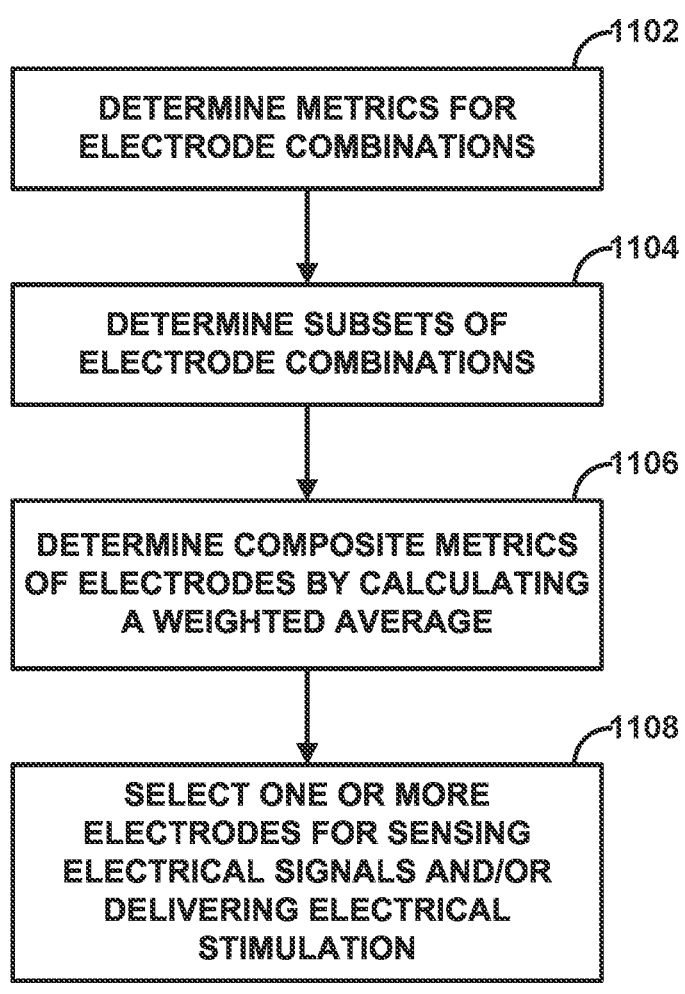
FIG. 11 is flow diagram of an example technique for determining a composite metric of an electrode using a weighted average of various types of electrode combinations, in accordance with one or more techniques of this disclosure.

FIG. 11 is flow diagram of an example technique for determining the composite metric of an electrode using a weighted average of various types of electrode combinations, in accordance with one or more techniques of this disclosure. Processing circuitry 80 of programmer 14 will be described for the example of FIG. 11, but any devices herein, or combinations of devices, may perform similar techniques of FIG. 11.

In the example of FIG. 11, processing circuitry 80 is configured to determine, for each respective electrode combination of a plurality of electrode combinations, a respective metric based on a sensed electrical signal from the respective electrode combination (1102). The sensed electrical signals may be LFPs, spectral power of a Beta frequency band within the sensed LFPs, a different type of electrical signal, an evoked signal from a delivered stimulus, or any other appropriate electrical signal generated by the brain.

Processing circuitry 80 is further configured to determine, for each respective (e.g., common) electrode of a plurality of electrodes, a subset of electrode combinations of the plurality of electrode combinations (1104). In this manner, each electrode combination of one subset of electrode combinations includes one electrode in common (e.g., common electrode). The subset of electrode combinations may include at least two electrode combinations. Processing circuitry 80 may determine a subset of electrode combinations for each electrode carried by a lead, or only some of the electrodes carried by the lead. In some examples, processing circuitry 80 may perform aspects of FIG. 11 in different orders or with one or more alternative features. For example, processing circuitry 80 may determine the subsets of electrode combinations (1104) prior to determining the metrics for each electrode combination (1102).

Processing circuitry 80 is further configured to determine, for each respective electrode of the plurality of electrodes, a respective composite metric based on the respective metrics of the subset of electrode combinations for that respective electrode by calculating a weighted average of the respective metrics of the subset of electrode combinations (1106). In some examples, processing circuitry 80 may multiply the respective average of each type (e.g., horizontal electrode combinations 1010, vertical electrode combinations 1012, ring electrode combinations 1014, diagonal electrode combinations, etc.) of electrode combinations by a respective weight to calculate the weighted average of the metrics. For example, processing circuitry 80 may multiply the average of horizontal combinations by a weight of 0.5, the average of vertical combinations by a weight of 0.25, and the ring combinations by a weight of 0.25. However, other weights may be used in other examples. Processing circuitry 80 may then add the weighted averages of horizontal electrode combinations, vertical electrode combinations, and ring electrode combinations to determine the composite metric of the common electrode of the horizontal, vertical, and ring electrode combinations. Processing circuitry 80 may determine the composite metric for each electrode of the plurality of electrodes of lead 1000 in a similar fashion.

Processing circuitry 80 may be further configured to select, based on the respective composite metrics of at least some electrodes of the plurality of electrodes, at least one electrode for at least one of sensing electrical signals or delivering electrical stimulation (1108). For example, processing circuitry 80 may select the electrode with the highest composite metric for delivering electrical stimulation, such as the cathode of an electrode combination with one or more additional electrodes. Processing circuitry 80 may perform the process of FIG. 10 and other techniques described in this disclosure. This disclosure includes various examples, such as the following examples.

Example 1

A system includes determine, for each respective electrode combination of a plurality of electrode combinations, a respective metric based on a sensed electrical signal from the respective electrode combination; determine, for each respective electrode of a plurality of electrodes, a subset of electrode combinations of the plurality of electrode combinations, each electrode combination of the subset of electrode combinations including the respective electrode, wherein the subset of electrode combinations includes at least two electrode combinations; determine, for each respective electrode of the plurality of electrodes, a respective composite metric based on the respective metrics of the subset of electrode combinations; and select, based on the respective composite metrics of the plurality of electrodes, at least one electrode for at least one of sensing electrical signals or delivering electrical stimulation.

Example 2

The system of example 1, wherein the processing circuitry is configured to control delivery of electrical stimulation using the selected at least one electrode.

Example 3

The system of example 1 or 2, further including sensing circuitry configured to generate the sensed electrical signals from the plurality of electrode combinations, wherein each electrode of the plurality of electrodes is carried by a medical lead.

Example 4

The system of example 3, wherein electrodes of the subset of electrode combinations are located at different axial positions along a length of the medical lead.

Example 5

The system of example 3 or 4, wherein electrodes of the subset of electrode combinations are located at different positions around a perimeter of the medical lead.

Example 6

The system of any of examples 1 through 5, wherein the sensed electrical signals include local field potentials.

Example 7

The system of example 6, wherein the processing circuitry is configured to determine each of the respective metrics based on a signal strength of the local field potentials.

Example 8

The system of any of examples 1 through 7, wherein the signal strength includes a spectral power of a Beta frequency band of local field potentials.

Example 9

The system of any of examples 1 through 8, wherein the processing circuitry is further configured to determine each of the respective composite metrics by averaging the respective metrics of the corresponding subset of electrode combinations.

Example 10

The system of example 9, wherein the subset of electrode combinations includes at least one horizontal electrode combination and at least one vertical electrode combination, wherein the horizontal electrode combination includes at least two electrodes located at different positions around a perimeter of the medical lead and located at the same axial positions along a length of the medical lead, and wherein the vertical electrode combination includes at least two electrodes located at the same positions around a perimeter of the medical lead and located at different axial positions along a length of the medical lead.

Example 11

The system of any of examples 1 through 10, wherein the subset of electrode combinations includes: a first electrode combination includes the first electrode at the first circumferential position around the perimeter of the medical lead; and a third electrode at a third circumferential position around the perimeter of the medical lead, the third circumferential position being different than the first circumferential position and the second circumferential position.

Example 12

The system of any of examples 1 through 11, wherein the processing circuitry is further configured to: determine a ranking of the plurality of electrodes based on the respective composite metrics; and select, based on the ranking, the at least one electrode for delivering the electrical stimulation.

Example 13

The system of any of examples 1 through 12, further including an implantable medical device including the processing circuitry.

Example 14

The system of any of examples 1 through 13, further including an external programmer including the processing circuitry, and wherein the external programmer is configured to transit the selected at least one electrode to an implantable medical device.

Example 15

A method includes determining, by processing circuitry and for each respective electrode combination of a plurality of electrode combinations, a respective metric based on a sensed electrical signal from the respective electrode combination; determining, by processing circuitry and for each respective electrode of a plurality of electrodes, a subset of electrode combinations of the plurality of electrode combinations, each electrode combination of the subset of electrode combinations including the respective electrode, wherein the subset of electrode combinations includes at least two electrode combinations; determining, by processing circuitry and for each respective electrode of the plurality of electrodes, a respective composite metric based on the respective metrics of the subset of electrode combinations; and selecting, by processing circuitry and based on the respective composite metrics of the plurality of electrodes, at least one electrode for at least one of sensing electrical signals or delivering electrical stimulation.

Example 16

The method of example 15, wherein the subset of electrode combinations includes at least one horizontal electrode combination and at least one vertical electrode combination, wherein the horizontal electrode combination includes at least two electrodes located at different positions around a perimeter of the medical lead and located at the same axial positions along a length of the medical lead, and wherein the vertical electrode combination includes at least two electrodes located at the same positions around a perimeter of the medical lead and located at different axial positions along a length of the medical lead.

Example 17

The method of example 16, wherein the processing circuitry determines the respective composite metric by calculating a weighted average, wherein the weighted average is, at least in part, calculated by multiplying the horizontal electrode combination by a first weight and multiplying the vertical electrode combination by a second weight.

Example 18

The method of any of examples 15 through 17, further including controlling, by processing circuitry, delivery of electrical stimulation using the selected at least one electrode.

Example 19

The method of any of examples 15 through 18, further including generating, by sensing circuitry, the sensed electrical signals from the plurality of electrode combinations, wherein each electrode of the plurality of electrodes is carried by a medical lead.

Example 20

The method of any of examples 15 through 19, wherein the sensed electrical signals include local field potentials.

Example 21

The method of any of examples 1 through 20, wherein the signal strength includes a spectral power of a Beta frequency band of the local field potentials.

Example 22

The method of any of examples 1 through 21, further including determining, by processing circuitry, a ranking of the respective composite metrics of the plurality of electrodes.

Example 23

A non-transitory computer-readable medium includes instructions that, when executed, cause processing circuitry to determine, for each respective electrode combination of a plurality of electrode combinations, a respective metric based on a sensed electrical signal from the respective electrode combination; determine, for each respective electrode of a plurality of electrodes, a subset of electrode combinations of the plurality of electrode combinations, each electrode combination of the subset of electrode combinations including the respective electrode, wherein the subset of electrode combinations includes at least two electrode combinations; determine, for each respective electrode of the plurality of electrodes, a respective composite metric based on the respective metrics of the subset of electrode combinations; and select, based on the respective composite metrics of the plurality of electrodes, at least one electrode for at least one of sensing electrical signals or delivering electrical stimulation.

As described herein, a system that employs directional brain sensing may reduce the time required to identify electrode combinations for sensing desired signals and/or delivering electrical stimulation therapy. In this manner, the systems described herein may improve clinician efficiency and treatment efficacy. This process is indeed advantageous considering the use of increasing number of electrodes on implantable leads (e.g., leads with electrodes disposed at different positions around the perimeter of the lead and at different positions along the length of the lead). Therefore, the techniques and systems described herein may enable the use of more electrodes that may improve targeting of desired tissue (e.g., specific regions of the brain associated with a disease, symptoms, or therapy) while reducing the time necessary for programming by the clinician.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other examples are within the scope of the following claims.

What is claimed is:

1. A system comprising:
   processing circuitry configured to:
      determine, for each respective electrode combination of a plurality of electrode combinations of a plurality of electrodes, a respective metric using a sensed electrical signal from the respective electrode combination;
      determine, for each single respective electrode of the plurality of electrodes, a subset of electrode combinations of the plurality of electrode combinations, each electrode combination of the subset of electrode combinations comprising the single respective electrode, wherein the subset of electrode combinations comprises at least two electrode combinations;
      calculate, for each single respective electrode of the plurality of electrodes, a respective composite metric using the respective metrics of the subset of electrode combinations determined using the sensed electrical signals from the respective electrode combinations;
      select, based on the respective composite metrics calculated for each single respective electrode of the plurality of electrodes, at least one electrode for at least one of sensing subsequent electrical signals or delivering electrical stimulation; and
      control at least one of:
         sensing, via sensing circuitry, the subsequent electrical signals using the selected at least one electrode, or
         delivering, via stimulation generation circuitry, electrical stimulation using the selected at least one electrode.

2. The system of claim 1, further comprising the sensing circuitry, wherein the sensing circuitry is configured to generate the sensed electrical signals from the plurality of electrode combinations, wherein each single electrode of the plurality of electrodes is carried by a medical lead.

3. The system of claim 1, wherein for each respective electrode combination, the sensed electrical signal comprises a local field potential.

4. The system of claim 3, wherein the processing circuitry is configured to determine each of the respective metrics using a signal strength of each of the local field potentials.

5. The system of claim 4, wherein the signal strength comprises a spectral power of a Beta frequency band of local field potentials.

6. The system of claim 1, wherein the processing circuitry is further configured to determine each of the respective composite metrics by averaging the respective metrics of the corresponding subset of electrode combinations.

7. The system of claim 6, wherein each single electrode of the plurality of electrodes is carried by a medical lead, and wherein the subset of electrode combinations comprises at least one horizontal electrode combination and at least one vertical electrode combination, wherein the at least one horizontal electrode combination comprises at least two electrodes located at different positions around a perimeter of the medical lead and located at the same axial positions along a length of the medical lead, and wherein the at least one vertical electrode combination comprises at least two electrodes located at the same positions around the perimeter of the medical lead and located at different axial positions along the length of the medical lead.

8. The system of claim 1, wherein each single electrode of the plurality of electrodes is carried by a medical lead, and wherein the subset of electrode combinations comprises:
   a first electrode combination comprising:
      a first electrode at a first circumferential position around a perimeter of the medical lead; and
      a second electrode at a second circumferential position around the perimeter of the medical lead, the second circumferential position being different than the first circumferential position; and
   a second electrode combination comprising:
      the first electrode at the first circumferential position around the perimeter of the medical lead; and
      a third electrode at a third circumferential position around the perimeter of the medical lead, the third circumferential position being different than the first circumferential position and the second circumferential position.

9. The system of claim 1, wherein the processing circuitry is further configured to:
   determine a ranking of the plurality of electrodes based on the respective composite metrics; and
   select, based on the ranking, the at least one electrode for delivering the electrical stimulation.

10. The system of claim 1, further comprising an implantable medical device comprising the processing circuitry.

11. The system of claim 1, further comprising an external programmer comprising the processing circuitry, and wherein the external programmer is configured to transmit the selected at least one electrode to an implantable medical device.

12. The system of claim 1, wherein the processing circuitry is configured to calculate, for each single respective electrode of the plurality of electrodes, the respective composite metric by at least applying a mathematical operation to the respective metrics of the subset of electrode combinations.

13. A method comprising:
   determining, by processing circuitry and for each respective electrode combination of a plurality of electrode combinations of a plurality of electrodes, a respective metric using a sensed electrical signal from the respective electrode combination;

determining, by the processing circuitry and for each single respective electrode of the plurality of electrodes, a subset of electrode combinations of the plurality of electrode combinations, each electrode combination of the subset of electrode combinations comprising the single respective electrode, wherein the subset of electrode combinations comprises at least two electrode combinations;

determining, by the processing circuitry and for each single respective electrode of the plurality of electrodes, a calculated respective composite metric using the respective metrics of the subset of electrode combinations determined using the sensed electrical signals from the respective electrode combinations;

selecting, by the processing circuitry and based on the calculated respective composite metrics of each single respective electrode of the plurality of electrodes, at least one electrode for at least one of sensing subsequent electrical signals or delivering electrical stimulation; and controlling, by the processing circuitry, at least one of:
    sensing, via sensing circuitry, the subsequent electrical signals using the selected at least one electrode, or
    delivering, via stimulation generation circuitry, electrical stimulation using the selected at least one electrode.

14. The method of claim 13, wherein each single electrode of the plurality of electrodes is carried by a medical lead, and wherein the subset of electrode combinations comprises at least one horizontal electrode combination and at least one vertical electrode combination, wherein the at least one horizontal electrode combination comprises at least two electrodes located at different positions around a perimeter of the medical lead and located at the same axial positions along a length of the medical lead, and wherein the at least one vertical electrode combination comprises at least two electrodes located at the same positions around the perimeter of the medical lead and located at different axial positions along the length of the medical lead.

15. The method of claim 14, wherein the processing circuitry determines the respective composite metric by calculating a weighted average, wherein the weighted average is, at least in part, calculated by multiplying the respective metric of the at least one horizontal electrode combination by a first weight and multiplying the respective metric of the at least one vertical electrode combination by a second weight.

16. The method of claim 13, further comprising generating, by the sensing circuitry, the sensed electrical signals from the plurality of electrode combinations, wherein each single electrode of the plurality of electrodes is carried by a medical lead.

17. The method of claim 13, wherein for each respective electrode combination, the sensed electrical signal comprises a local field potential, the method further comprising:
    determining, by the processing circuitry, each of the respective metrics using a signal strength of each of the local field potentials, the signal strength comprising a spectral power of a Beta frequency band of the local field potentials.

18. The method of claim 13, further comprising determining, by the processing circuitry, a ranking of the respective composite metrics of the plurality of electrodes.

19. A non-transitory computer-readable medium comprising instructions that, when executed, cause processing circuitry to:
    determine, for each respective electrode combination of a plurality of electrode combinations of a plurality of electrodes, a respective metric using a sensed electrical signal from the respective electrode combination;
    determine, for each single respective electrode of the plurality of electrodes, a subset of electrode combinations of the plurality of electrode combinations, each electrode combination of the subset of electrode combinations comprising the respective electrode, wherein the subset of electrode combinations comprises at least two electrode combinations;
    determine, for each respective electrode of the plurality of electrodes, a calculated respective composite metric using the respective metrics of the subset of electrode combinations determined using the sensed electrical signals from the respective electrode combinations;
    select, based on the calculated respective composite metrics of each respective electrode of the plurality of electrodes, at least one electrode for at least one of sensing subsequent electrical signals or delivering electrical stimulation; and
    control at least one of:
        sensing, via sensing circuitry, the subsequent electrical signals using the selected at least one electrode, or
        delivering, via stimulation generation circuitry, electrical stimulation using the selected at least one electrode.

* * * * *